United States Patent [19]
Nestor, Jr. et al.

[11] Patent Number: 4,801,577
[45] Date of Patent: Jan. 31, 1989

[54] NONAPEPTIDE AND DECAPEPTIDE ANALOGS OF LHRH USEFUL AS LHRH ANTAGONISTS

[75] Inventors: John J. Nestor, Jr., San Jose; Brian H. Vickery, Saratoga, both of Calif.

[73] Assignee: Syntex (U.S.A.) Inc., Palo Alto, Calif.

[21] Appl. No.: 10,923

[22] Filed: Feb. 5, 1987

[51] Int. Cl.$^4$ .................... C07K 7/20; A61K 37/43
[52] U.S. Cl. ........................ 514/15; 514/800; 530/313; 530/328
[58] Field of Search ............ 530/328, 313; 514/15, 514/800

[56] References Cited

U.S. PATENT DOCUMENTS

| | | | |
|---|---|---|---|
| 4,215,038 | 7/1980 | Rivier et al. | 530/313 |
| 4,341,767 | 7/1982 | Nestor et al. | 530/313 |
| 4,419,347 | 12/1983 | Nestor et al. | 530/313 |
| 4,481,190 | 11/1984 | Nestor et al. | 530/313 |
| 4,569,927 | 2/1986 | Rivier et al. | 530/328 |
| 4,581,169 | 4/1986 | Nestor et al. | 530/313 |
| 4,667,014 | 5/1987 | Nestor et al. | 514/800 |
| 4,690,916 | 9/1987 | Nestor et al. | 514/800 |

OTHER PUBLICATIONS

Karten et al., "In Vitro Histamine Release with LHRH Analogs", *LHRH and its Analogs, Contraceptive and Therapeutic Applications,* part 2 (1987).

Roeske et al., "LHRH Antagonists with Low Histamine Releasing Activity", *LHRH and its Analogs, Contraceptive and Therapeutic Applications,* part 2 (1987).

*Primary Examiner*—Morton Foelak
*Assistant Examiner*—Christina Chan
*Attorney, Agent, or Firm*—Liza K. Toth; Tom M. Moran; Alan M. Krubiner

[57] ABSTRACT

Synthetic nona- and decapeptide LHRH antagonist analogs are disclosed, having a sterically hindered guanidino-substituted arginyl or homoarginyl residue at position 8, with no arginyl substituent at position 6.

41 Claims, No Drawings

NONAPEPTIDE AND DECAPEPTIDE ANALOGS OF LHRH USEFUL AS LHRH ANTAGONISTS

BACKGROUND OF THE INVENTION

Luteinizing hormone (LH) and follicle stimulating hormone (FSH) are released from the anterior pituitary gland under the control of luteinizing releasing hormone (LHRH) produced in the hypothalamic region. LH and FSH act on the gonads to stimulate the synthesis of steroid hormones and to stimulate gamete maturation. The pulsatile release of LHRH, and thereby the release of LH and FSH, controls the reproductive cycle in domestic animals and humans.

LHRH also affects the placenta, and therefore the gonads indirectly, by causing the synthesis and release of chorionic gonadotropin (CG).

Antagonists of LHRH are useful for the control of fertility. Such antagonists block ovulation in the female and suppress spermatogenesis in the male. Related to these effects is a suppression of normal circulating levels of sexual steroids of gonadal origin, causing reduction in accessory organ weight in the male and the female. In domestic animals this effect suppresses sexual cycling and behavior (promoting weight gain in a feed-lot situation), induces abortion in pregnant animals, and in general, acts as a chemical sterilant.

The natural releasing hormone LHRH is a decapeptide comprised of naturally occuring amino acids (which have the L-configuration except for the achiral amino acid glycine). Its sequence is as follows:

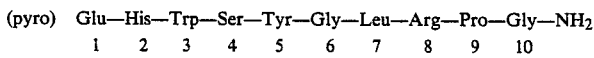

(pyro) Glu—His—Trp—Ser—Tyr—Gly—Leu—Arg—Pro—Gly—NH$_2$
  1   2   3   4   5   6   7   8   9   10

Analogs of this natural material are often described in abbreviated form by showing the nature of the substituent of a given amino acid, superscribed by its location, followed by "LHRH." Many analogs of LHRH have been studied, and a very large majority are of insufficient biological activity to be clinically useful. However, certain select modifications have a potentiating effect on agonist biological activity. A significant enhancement to agonist activity is obtained by changing the 6-position residue from Gly to a D-amino acid.

In addition to agonists, analogs have been prepared which are competitive antagonists to LHRH, all of which require deletion or replacement of the histidyl residue at position 2: Vale, W., et al., *Science*, 176: 933 (1972). In general, it appears that a D-amino acid placed in the sequence at that position gives the best activity: Rees, R. W. A., et al., *J. Med. Chem.* 17: 1016 (1974).

Moreover, adding a modification at the 6 position (which, without the modification at position 2, results in the agonist activity cited above) enhances the antagonist activity of the 2-modified analogs: Beattie, C. W., et al, *J. Med. Chem.*, 18: 1247 (1975); Rivier, J., et al., *Peptides* 1976 p. 427, Editions de l'Universite de Bruxelles, Belgium (1976).

Against the background of these two major alterations, which result in more potent LHRH antagonists, additional increments in antagonist activity may be had by modifying positions 1, 3, 5 and/or 10 in the already 2, 6 modified peptide. Coy, D. H., et al *Peptides* 1976, p. 462, Editions de l'Universite de Bruxelles, Belgium (1976); Rivier, J. E., et al, *Life Sci.* 23: 869 (1978); Dutta, A. S., et al, *Biochem Biophys. Res. Commun.* 81: 382 (1978), Humphries, J., et al, *Biochem. Biophys. Res. Commun.*, 85: 709 (1978). It has also been shown that N-acylation of the amino acid at position 1 is helpful; Channabasavaia, K., et al, *Biochem. Biophys. Res. Commun.* 81: 382 (1978); Coy, D. H., et al, *Peptides.—Structure and Biological Function* p. 775, Pierce Chemical Co. (1979). Additionally, a highly potent antagonist containing a D-Arg[6] substitution, (N-Ac-D-pCl-Phe[1], D-pCl-Phe[2], D-Trp[3], D-Arg[6], D-Ala[10])LHRH, has been published by D. H. Coy, *Endocrinology*, 110, 1445 (1982).

Unfortunately, although the class of LHRH analogs containing a D-Arg[6] substitution were found to be potent antiovulatory substances, they were also potent mast cell degranulating substances, Schmidt et al., *Contraception*, 29, 283 (1984), and caused edema in vivo. Thus, for example, (N-Ac-D-Nal(2)[1], D-pCl-Phe[2], D-Trp[3], D-Arg[6])LHRH has an ED$_{50}$=0.2 μg/ml for histamine release from rat mast cells in vitro. This side reaction is of clinical importance because of the potential life threatening nature of the ensuing anaphylactoid reaction.

It is well known in the art that molecules containing positive charge(s), especially multiple positive charges, in association with hydrophobicity are potent mast cell degranulators: Foreman and Jordan, *Agents and Actions*, 13, 105 (1983). An initial attempt to circumvent this problem in analogs containing two Arg residues (i.e., in positions 6 and 8) was to increase the space between the residues (e.g., (N-Ac-D-Nal(2)[1], D-pCl-Phe[2], D-Trp[3], Arg[5], D-Tyr[6], D-Ala[10])LHRH, (ED$_{50}$=2 μg/ml for histamine release, R. Roeske, personal communication). While this led to a decrease in the potency of the analog for degranulation of mast cells and release of histamine, the analog still had many fold greater anaphylactoid potency than LHRH, for which ED$_{50}$ is 328 μg/ml for histamine release.

R. Roeske (personal communication) has incorporated Lys(iPr) into positions 6 and 8 in conjunction with a D-pCl-Phe residue in position 2 with retention of high antiovulatory potency and decreased histamine release (e.g., (N-Ac-D-Nal(2)[1], pCl-Phe[2], D-Trp[3], D-Lys(iPr)[8], Lys(iPr)[6], D-Ala[10])LHRH; ED$_{50}$=6.6 μg/ml for histamine release). In one analog, hArg(Et$_2$) was incorporated into position 8 with a similar degree of histamine release potency (i.e., (N-Ac-D-Nal(2)[1], D-αMe-pCl-Phe[2], D-Pal(3)[3], D-Arg[6], hArg(Et$_2$)[8], D-Ala[10])LHRH; ED$_{50}$=4.9 μg/ml for histamine release). However, it can be seen that these analogs are still potent histamine releasing agents compared to LHRH.

Thus, the presently known set of analogs still has significant possibility for toxicity and other side effects.

SUMMARY OF THE INVENTION

The present invention refers to novel, highly potent nonapeptide and decapeptide analogs of LHRH with minimal histamine releasing potency for which a replacement at position 8 by a sterically hindered guanidino-substituted arginyl residue, coupled with avoidance of an arginyl substituent at position 6, is a critical feature. The invention is also directed to various methods of use of these compounds and to pharmaceutical compositions therefor.

More specifically, the present invention relates to compounds of the formula

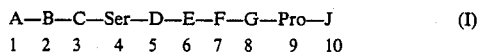 (I)

or a pharmaceutically acceptable salt thereof, wherein:

A is an amino acyl residue selected from the group consisting of either the D- or the L-isomer of: N-Ac-D,L-$\Delta^{3,4}$-prolyl, N-Ac-D,L-prolyl, N-Ac-D,L-phenylalanyl, N-Ac-D,L-p-chlorophenylalanyl, N-Ac-D,L,-p-fluorophenylalanyl, N-Ac-3-(1-naphthyl)-D,L-alanyl, N-Ac-3-(2-naphthyl)-D,L-alanyl, and N-Ac-3-(2,4,6-trimethylphenyl)-D,L-alanyl;

B is an amino acyl residue selected from the group consisting of D-phenylalanyl, D-p-chlorophenylalanyl, D-p-fluorophenylalanyl, D-p-nitrophenylalanyl, 2,2-diphenylglycol, D-α-methyl-p-chlorophenylalanyl and 3-(2-naphthyl)-D-alanyl;

C is an amino acyl residue selected from the group consisting of D-tryptophanyl, D-phenylalanyl, 3-(3-pyridyl)-D-alanyl, and 3-(2-naphthyl)-D-alanyl;

D is an amino acyl residue selected from the group consisting of L-phenylalanyl, L-tyrosyl, and 3-(3-pyridyl)-alanyl, arginyl, or G;

E is 3-(2-naphthyl)-D-alanyl, 3-(3-pyridyl)-D-alanyl, D-tyrosyl, D-tryptophanyl, D-nicotinyl-lysyl, pyridylacetyl-lysyl, D-Glu(AA) or G;

F is an amino acyl residue selected from the group consisting of L-leucyl, L-norleucyl, L-phenylalanyl, L-tryptophanyl, and 3-(2-naphthyl)-L-alanyl;

G is an amino acyl residue selected from the group consisting of the radicals represented by the following structural formulas:

(a) 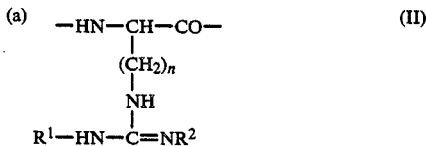 (II)

wherein
n is 1 to 5;
$R^1$ is alkyl of 1 to 6 carbon atoms or fluoroalkyl;
$R^2$ is hydrogen or $R^1$; or $R^1$—HN—C≡NR² is a ring represented by the following structural formulas:

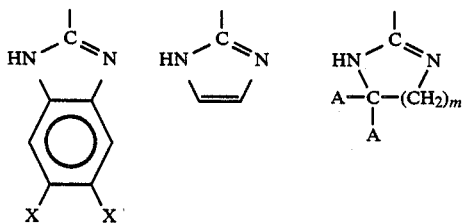

wherein m is 1 to 4; A is hydrogen or alkyl of 1 to 6 carbon atoms; and X is halo or A; and (b) 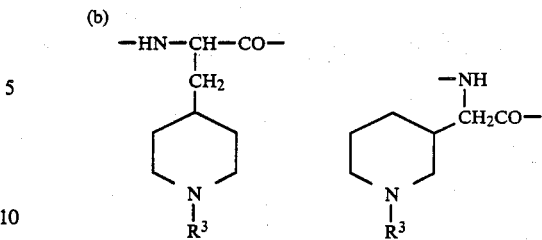

wherein
$R^3$ is hydrogen, alkyl of 1 to 6 carbon atoms, phenyl or phenylloweralkyl; and
J is D-alaninamide; D-leucinamide; glycinamide; or —$NHR^4$ wherein $R^4$ is lower alkyl or $NHCONH_2$.

Another aspect of the invention relates to a method of treating endometriosis in a female mammalian subject, which method comprises administering to said subject an effective amount of a compound of Formula I or a pharmaceutical composition containing an effective amount of a compound of Formula I.

Still another aspect of the invention relates to a method of treating prostatic hypertrophy in a male mammalian subject, which method comprises administering to said subject an effective amount of the compound of Formula I or a pharmaceutical composition containing an effective amount of the compound of Formula I.

Yet another aspect of the invention relates to a method of treating precocious puberty in a human subject, which method comprises administering to said subject an effective amount of the compound of Formula I or a pharmaceutical composition containing an effective amount of the compound of Formula I.

A further aspect of the invention relates to a method of interrupting heat in an animal, which method comprises administering to said animal an effective amount of the compound of Formula I or a pharmaceutical composition containing an effective amount of the compound of Formula I.

A still further aspect of the invention relates to a method of terminating pregnancy in an animal, which method comprises administering to said animal an effective amount of the compound of Formula I or a pharmaceutical composition containing an effective amount of the compound of Formula I.

An additional aspect of the invention relates to a method of inhibiting spermatogenesis in a male mammalian subject, which method comprises administering to said subject an effective amount of the compound of Formula I or a pharmaceutical composition containing an effective amount of the compound of Formula I.

Another important aspect of the invention relates to a method of preventing ovarian hyperstimulation in response to exogenous gonadotropins in a human female, which method comprises administering to said subject an effective amount of the compound of Formula I or a pharmaceutical composition containing an effective amount of the compound of Formula I.

An additional important aspect of the invention relates to a method of treating premenstrual syndrome in a human female, which method comprises administering to said subject an effective amount of the compound of Formula I or a pharmaceutical composition containing an effective amount of the compound of Formula I.

A still additional aspect of the invention relates to a method for preventing ovulation in a human female, which method comprises administering to said subject an effective amount of the compound of Formula I or a pharmaceutical composition containing an effective amount of the compound of Formula I.

A final aspect of the invention relates to a pharmaceutical composition for inhibiting ovulation in a mammalian female subject; preventing ovarian hyperstimulation in response to exogenous gonadotropins, treating premenstrual syndrome, or treating endometriosis in a female human subject; for treating prostatic hypertrophy or inhibiting spermatogenesis in a male mammalian subject; or for treating precocious puberty in a human subject; or interrupting heat in a female animal; or terminating pregnancy in a female mammalian subject; comprising an effective amount of the compound of Formula I in admixture with at least one pharmaceutically acceptable excipient.

DETAILED DESCRIPTION OF THE INVENTION

The replacement of the L-histidyl residue which is at position 2 in LHRH with one of the residues herein specified is a requirement to convert the peptide to an LHRH antagonist. The replacement of the glycyl residue at position 6 in LHRH with one of the residues specified as E gives a dramatic enhancement of the antagonist effect. The substitutions disclosed herein at positions 1, 2, 3, 5, 7 and 10 are further helpful in enhancing the antagonist activity. The substitution G in position 8 provides a profound diminution in the histamine releasing potency of the analogs when the substitution in position 6 is other than Arg, and is critical for their use as safe drugs.

ABBREVIATIONS AND DEFINITIONS

As set forth above, and for convenience in describing this invention, the conventional abbreviations for the various common amino acids are used as generally accepted in the peptide art as recommended by the IUPAC-IUB Commission on Biochemical Nomenclature, *Biochemistry*, 11, 1726 (1972). All peptide sequences mentioned herein are written according to the generally accepted convention whereby the N-terminal amino acid is on the left and the C-terminal amino acid is on the right.

The abbreviations herein represent L-amino acids, with the exception of the achiral amino acid glycine, and with the further exception of any unnatural or natural amino acids which are achiral, or are otherwise designated as D- or D,L-.

It should be noted that when $J=NH-C(O)-NH_2$, the C-terminus is an aza-glycinamide residue.

The abbreviation D-Glu(AA) represents the anisole adduct to a D-Glu residue to form a para-methoxyphenylketone (at the carboxyl terminus of the glutamic acid side chain), i.e., Glu(pMeO-Ph).

Certain other abbreviations will be useful in describing the invention. The present invention employs replacements of amino acids in the natural LHRH peptide by amino acids which do not occur in nature. Particularly commonly employed among these are the following:

| Amino acid residue | Abbreviation |
| --- | --- |
| 3-(2-naphthyl)-alanyl | Nal(2) |//

| Amino acid residue | Abbreviation |
| --- | --- |
| 3-(p-fluorophenyl)-alanyl | pF—Phe |
| 3-(p-chlorophenyl)-alanyl | pCl—Phe |
| 3-(3-pyridyl)-alanyl | Pal(3) |
| N,N'—guanidino-dimethyl-homoarginyl | Dmh, or hArg(Me)$_2$ |
| N,N'—guanidino-(diethyl)-homoarginyl | Deh, or hArg(Et)$_2$ |
| N,N'—guanidino-(dipropyl)-homoarginyl | Dph, or hArg(Pr)$_2$ |
| N,N'—guanidino-(diisopropyl)-homoarginyl | Dih, or Arg (iPr)$_2$ |
| N,N'—guanidino-(dihexyl)-homoarginyl | Dhh, or hArg(hexyl)$_2$ |
| N,N'—guanidino-(ethano)-homoarginyl | Eha or hArg(CH$_2$)$_2$ |
| N,N'—guanidino-(propano)-homoarginyl | Pha, or hArg(CH$_2$)$_3$ |
| N,N'—guanidino-bis-(2,2,2-trifluoroethyl)-homoarginyl | Bth, or hArg(CH$_2$CF$_3$)$_2$ |
| N—guanidino-(ethyl)-homoarginyl | Meh, or hArg(Et) |
| N—guanidino-(propyl)-homoarginyl | Prh, or hArg(propyl) |
| N—guanidino-(isopropyl)-homoarginyl | Iph, or hArg(iPr) |
| N—guanidino-(butyl)-homoarginyl | Mbh, or hArg(Bu) |
| N,N'—guanidino-(dicyclohexyl)-homoarginyl | Dch, or hArg(cyclohexyl)$_2$ |
| N—guanidino-(heptyl)-homoarginyl | Hha, or hArg(heptyl) |
| N—guanidino-(ethyl)-arginyl | Mea, or Arg(Et) |
| N,N'—guanidino-(diisopropyl)-arginyl | Dia, or Arg(iPr)$_2$ |
| N,N'—guanidino-(dicyclohexyl)-arginyl | Dca, or Arg(cyclohexyl)$_2$ |
| 3-(3-piperidyl)-alanyl | 3-Pia |
| 3-(4-piperidyl)-alanyl | 4-Pia |
| 3-((N$^\epsilon$—methyl)piperid-4-yl)-alanyl | Mpa |
| 3-((N$^\epsilon$—pentyl)piperid-4-yl)-alanyl | Ppa |
| 3-((N$^\epsilon$—benzyl)piperid-4-yl)-alanyl | Bpa |
| N$^\epsilon$—Nicotinyl-D-lysyl | Lys(Nic) |
| N$^\epsilon$—(3-Pyridyl)acetyl-D-lysyl | Lys(pyridylacetyl) |
| 3-(2,4,6-trimethylphenyl)alanyl | Tmp |
| 2,2-diphenylglycyl | Dpg |

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylene-diamine or ethylenediamine; or (c) combinations, of (a) and (b), e.g., a zinc tannate salt and the like.

The term "lower alkyl" refers to a straight or branched chain saturated hydrocarbon radical having from 1 to 4 carbon atoms such as, for example, methyl, ethyl, n-propyl, isopropyl, n-butyl, isobutyl, sec-butyl and tert-butyl. "Alkyl of 1 to 6 carbon atoms" encompasses the same substituents as lower alkyl but in addition includes radicals having 5 or 6 carbon atoms such as, for example, n-pentyl, n-hexyl or branched 5 or 6 carbon membered radicals. "Alkyl of 1 to 12 carbon atoms" comprises a hydrocarbon radical of 1 to 12 carbon atoms including the radicals noted above, except that the radical may have up to 12 carbon atoms.

Fluoroalkyl refers to lower alkyl substituted with 1 to 5 fluorine atoms, for example $CF_3CH_2-$, $CF_3-$, $CF_3CF_2CH_2-$, and the like.

Halo refers to fluoro, chloro or bromo.

The abbreviation "N-Ac" refers specifically to the N-acetyl protecting group, i.e., an acetyl group attached to a terminal amino acid residue on the amine nitrogen, in conformance with generally accepted nomenclature.

PREFERRED EMBODIMENTS

Compounds which are preferred embodiments of the present invention are those wherein A is N-Ac-D-Nal(2) or N-Ac-D-pCl-Phe; B is D-pF-Phe or D-pCl-Phe; C is D-Trp, D-Nal(2) or Pal(3); D is Pal(3), Tyr, Arg, Deh, Mbh, Bth, or Pha; E is D-Trp, D-Tyr, D-Nal(2), D-Pal(3), D-Deh, D-Mbh, D-Pha or D-Bth; F is Leu or Phe; G is Deh, Bth, Mbh, or Pha; and J is D-AlaNH₂ or GlyNH₂.

More preferred substitution patterns are those wherein:
A is N-Ac-D-Nal(2);
B is D-pCl-Phe;
C is D-Trp or D-Pal(3);
D is Tyr, Arg, Deh, Mbh, Bth or Pha;
E is D-Trp, D-Pal(3), D-Nal(2), D-Tyr, D-Deh, D-Mbh, D-Bth or D-Pha;
F is Leu;
G is Deh, Mbh, Bth and Pha; and
J is D-AlaNH₂.

There are three preferred subclasses within this more preferred class:
1. When D is Tyr, E can be any one of either (a) the hydrophobic residues D-Trp, D-Pal(3), D-Nal(2) or D-Tyr, but most preferably D-Trp or D-Pal(3), or (b) the residues D-Deh, D-Mbh, D-Bth or D-Pha;
2. When D is Arg, E is preferably one of the hydrophobic residues listed in 1(a) above, and most preferably D-Tyr;
3. When D is any of Deh, Mbh, Bth or Pha, E is most preferably D-Tyr or D-Pal(3), but D-Nal(2) and D-Trp are also preferred.
In each of the preferred subclasses, G is Deh, Mbh, Bth or Pha. Particularly preferred are Bth and Deh, and most particularly, Bth.

Thus, examples of the more preferred substitution patterns are:
N-Ac-D-Nal(2)-D-pCl-Phe-C-Ser-Tyr-C-Leu-G-Pro-D-AlaNH₂, wherein C is D-Trp or D-Pal(3) and G is Deh, Mbn, Bth or Pha;
N-Ac-D-Nal(2)-D-pCl-Phe-C-Ser-Tyr-E-Leu-G-Pro-D-AlaNH₂, wherein C is D-Trp or D-Pal(3), E is D-Deh, D-Bth, D-Mbh or D-Pha, and G is the L-form of E as defined in this paragraph;
N-Ac-D-Nal(2)-D-pCl-Phe-C-Ser-Arg-E-Leu-G-Pro-D-AlaNH₂, wherein C is D-Trp or D-Pal(3), E is D-Trp, D-Pal(3), D-Nal(2), or D-Tyr, and G is Deh, Mbh, Bth or Pha; and
N-Ac-D-Nal(2)-D-pCl-Phe-C-Ser-D-E-Leu-G-Pro-D-AlaNH₂, wherein C is D-Trp or D-Pal(3), D and G are independently Deh, Bth, Mbh or Pha, and E is D-Tyr, D-Nal(2), D-Trp or D-Pal(3).

Additional preferred embodiments are those wherein:
N-Ac-D-Nal(2)-D-pCl-Phe-D-Trp-Ser-Tyr-E-Leu-G-Pro-D-AlaNH₂, wherein E is D-Trp, D-Tyr, or D-Nal(2) and G is Deh, Bth, Mbh, or Pha;
N-Ac-D-Nal(2)-D-pCl-Phe-C-Ser-D-E-Leu-G-Pro-D-AlaNH₂, wherein D and G are independently Deh, Bth, Mbh or Pha, and both C and E are independently D-Trp or D-Pal(3); and
N-Ac-D-Nal(2)-D-pCl-Phe-D-Pal(3)-Ser-Tyr-D-Pal(3)-Leu-G-Pro-D-AlaNH₂, wherein G is Deh, Bth, Mbh, or Pha.

Exemplary preferred embodiments are:
N-Ac-D-Nal(2)-D-pCl-Phe-D-Pal(3)-Ser-Tyr-D-Pal(3)-Leu-Deh-Pro-D-AlaNH₂;
N-Ac-D-Nal(2)-D-pCl-Phe-D-Pal(3)-Ser-Tyr-D-Pal(3)-Leu-Bth-Pro-D-AlaNH₂;
N-Ac-D-Nal(2)-D-pCl-Phe-D-Pal(3)-Ser-Tyr-D-Pal(3)-Leu-Mbh-Pro-D-AlaNH₂;
N-Ac-D-Nal(2)-D-pCl-Phe-D-Pal(3)-Ser-Tyr-D-Pal(3)-Leu-Pha-Pro-D-AlaNH₂;
N-Ac-D-Nal(2)-D-pCl-Phe-D-Trp-Ser-Tyr-D-Trp-Leu-Deh-Pro-D-AlaNH₂;
N-Ac-D-Nal(2)-D-pCl-Phe-D-Trp-Ser-Tyr-D-Trp-Leu-Bth-Pro-D-AlaNH₂;
N-Ac-D-Nal(2)-D-pCl-Phe-D-Trp-Ser-Tyr-D-Trp-Leu-Mbh-Pro-D-AlanNH₂;
N-Ac-D-Nal(2)-D-pCl-Phe-D-Trp-Ser-Tyr-D-Trp-Leu-Pha-Pro-D-AlaNH₂;
N-Ac-D-Nal(2)-D-pCl-Phe-D-Trp-Ser-Tyr-D-Deh-Leu-Deh-Pro-D-AlaNH₂;
N-Ac-D-Nal(2)-D-pCl-Phe-D-Trp-Ser-Tyr-D-Mbh-Leu-Mbh-Pro-D-AlaNH₂;
N-Ac-D-Nal(2)-D-pCl-Phe-D-Trp-Ser-Tyr-D-Bth-Leu-Bth-Pro-D-AlaNH₂;
N-Ac-D-Nal(2)-D-pCl-Phe-D-Trp-Ser-Tyr-D-Pha-Leu-Pha-Pro-D-AlaNH₂;
N-Ac-D-Nal(2)-D-pCl-Phe-D-Pal(3)-Ser-Tyr-D-Deh-Leu-Deh-Pro-D-AlaNH₂;
N-Ac-D-Nal(2)-D-pCl-Phe-D-Pal(3)-Ser-Tyr-D-Mbh-Leu-Mbh-Pro-D-AlaNH₂;
N-Ac-D-Nal(2)-D-pCl-Phe-D-Pal(3)-Ser-Tyr-D-Bth-Leu-Bth-Pro-D-AlaNH₂;
N-Ac-D-Nal(2)-D-pCl-Phe-D-Pal(3)-Ser-Tyr-D-Pha-Leu-Pha-Pro-D-AlaNH₂;
N-Ac-D-Nal(2)-D-pCl-Phe-D-Trp-Ser-Arg-D-Trp-Leu-Deh-Pro-D-AlaNH₂;
N-Ac-D-Nal(2)-D-pCl-Phe-D-Trp-Ser-Arg-D-Trp-Leu-Bth-Pro-D-AlaNH₂;
N-Ac-D-Nal(2)-D-pCl-Phe-D-Trp-Ser-Arg-D-Trp-Leu-Mbh-Pro-D-AlaNH₂;
N-Ac-D-Nal(2)-D-pCl-Phe-D-Trp-Ser-Arg-D-Trp-Leu-Pha-Pro-D-AlaNH₂;
N-Ac-D-Nal(2)-D-pCl-Phe-D-Pal(3)-Ser-Arg-D-Pal(3)-Leu-Bth-Pro-D-AlaNH₂;
N-Ac-D-Nal(2)-D-pCl-Phe-D-Pal(3)-Ser-Arg-D-Pal(3)-Leu-Mbh-Pro-D-AlaNH₂;
N-Ac-D-Nal(2)-D-pCl-Phe-D-Pal(3)-Ser-Arg-D-Pal(3)-Leu-Deh-Pro-D-AlaNH₂;
N-Ac-D-Nal(2)-D-pCl-Phe-D-Pal(3)-Ser-Arg-D-Pal(3)-Leu-Pha-Pro-D-AlaNH₂;
N-Ac-D-Nal(2)-D-pCl-Phe-D-Trp-Ser-Arg-D-Tyr-Leu-Deh-Pro-D-AlaNH₂;
N-Ac-D-Nal(2)-D-pCl-Phe-D-Trp-Ser-Arg-D-Tyr-Leu-Bth-Pro-D-AlaNH₂;
N-Ac-D-Nal(2)-D-pCl-Phe-D-Trp-Ser-Arg-D-Tyr-Leu-Mbh-Pro-D-AlaNH₂;

N-Ac-D-Nal(2)-D-pCl-Phe-D-Trp-Ser-Arg-D-Tyr-Leu-Pha-Pro-D-AlaNH$_2$;
N-Ac-D-Nal(2)-D-pCl-Phe-D-Pal(3)-Ser-Arg-D-Tyr-Leu-Bth-Pro-D-AlaNH$_2$;
N-Ac-D-Nal(2)-D-pCl-Phe-D-Pal(3)-Ser-Arg-D-Tyr-Leu-Mbh-Pro-D-AlaNH$_2$;
N-Ac-D-Nal(2)-D-pCl-Phe-D-Pal(3)-Ser-Arg-D-Tyr-Leu-Deh-Pro-D-AlaNH$_2$;
N-Ac-D-Nal(2)-D-pCl-Phe-D-Pal(3)-Ser-Arg-D-Tyr-Leu-Pha-Pro-D-AlaNH$_2$;
N-Ac-D-Nal(2)-D-pCl-Phe-D-Trp-Ser-Deh-D-Tyr-Leu-Deh-Pro-D-AlaNH$_2$;
N-Ac-D-Nal(2)-D-pCl-Phe-D-Trp-Ser-Mbh-D-Tyr-Leu-Mbh-Pro-D-AlaNH$_2$;
N-Ac-D-Nal(2)-D-pCl-Phe-D-Trp-Ser-Bth-D-Tyr-Leu-Bth-Pro-D-AlaNH$_2$;
N-Ac-D-Nal(2)-D-pCl-Phe-D-Trp-Ser-Pha-D-Tyr-Leu-Pha-Pro-D-AlaNH$_2$;
N-Ac-D-Nal(2)-D-pCl-Phe-D-Trp-Ser-Deh-D-Trp-Leu-Deh-Pro-D-AlaNH$_2$;
N-Ac-D-Nal(2)-D-pCl-Phe-D-Trp-Ser-Mbh-D-Trp-Leu-Mbh-Pro-D-AlaNH$_2$;
N-Ac-D-Nal(2)-D-pCl-Phe-D-Trp-Ser-Bth-D-Trp-Leu-Bth-Pro-D-AlaNH$_2$;
N-Ac-D-Nal(2)-D-pCl-Phe-D-Trp-Ser-Pha-D-Trp-Leu-Pha-Pro-D-AlaNH$_2$;
N-Ac-D-Nal(2)-D-pCl-Phe-D-Pal(3)-Ser-Deh-D-Pal(3)-Leu-Deh-Pro-D-AlaNH$_2$;
N-Ac-D-Nal(2)-D-pCl-Phe-D-Pal(3)-Ser-Mbh-D-Pal(3)-Leu-Mbh-Pro-D-AlaNH$_2$;
N-Ac-D-Nal(2)-D-pCl-Phe-D-Pal(3)-Ser-Bth-D-Pal(3)-Leu-Bth-Pro-D-AlaNH$_2$;
N-Ac-D-Nal(2)-D-pCl-Phe-D-Pal(3)-Ser-Pha-D-Pal(3)-Leu-Pha-Pro-D-AlaNH$_2$;
N-Ac-D-Nal(2)-D-pCl-Phe-D-Trp-Ser-Deh-D-Nal(2)-Leu-Deh-Pro-D-AlaNH$_2$;
N-Ac-D-Nal(2)-D-pCl-Phe-D-Trp-Ser-Mbh-D-Nal(2)-Leu-Mbh-Pro-D-AlaNH$_2$;
N-Ac-D-Nal(2)-D-pCl-Phe-D-Trp-Ser-Bth-D-Nal(2)-Leu-Bth-Pro-D-AlaNH$_2$;
N-Ac-D-Nal(2)-D-pCl-Phe-D-Trp-Ser-PHa-D-Nal(2)-Leu-Pha-Pro-D-AlaNH$_2$;
N-Ac-D-Nal(2)-D-pCl-Phe-D-Pal(3)-Ser-Pal(3)-D-Pal(3)-Leu-Deh-Pro-D-AlaNH$_2$;
N-Ac-D-Nal(2)-D-pCl-Phe-D-Pal(3)-Ser-Pal(3)-D-Pal(3)-Leu-Bth-Pro-D-AlaNH$_2$;
N-Ac-D-Nal(2)-D-pCl-Phe-D-Pal(3)-Ser-Pal(3)-D-Pal(3)-Leu-Pha-Pro-D-AlaNH$_2$;
N-Ac-D-Nal(2)-D-pCl-Phe-D-Pal(3)-Ser-Pal(3)-D-Pal(3)-Leu-Mbh-Pro-D-AlaNH$_2$;
N-Ac-D-Nal(2)-D-pCl-Phe-D-Pal(3)-Ser-Tyr-D-Mbh-Leu-Bth-Pro-D-AlaNH$_2$;
N-Ac-D-Nal(2)-D-pCl-Phe-D-Trp-Ser-Tyr-D-Mbh-Leu-Bth-Pro-D-AlaNH$_2$;
N-Ac-D-Nal(2)-D-pF-Phe-D-Pal(3)-Ser-Tyr-D-Pal(3)-Leu-Deh-Pro-D-AlaNH$_2$;
N-Ac-D-Nal(2)-D-pF-Phe-D-Pal(3)-Ser-Tyr-D-Pal(3)-Leu-Bth-Pro-D-AlaNH$_2$;
N-Ac-D-Nal(2)-D-pF-Phe-D-Trp-Ser-Tyr-D-Trp-Leu-Deh-Pro-D-AlaNH$_2$;
N-Ac-D-Nal(2)-D-pF-Phe-D-Trp-Ser-Tyr-D-Trp-Leu-Bth-Pro-D-AlaNH$_2$;
N-Ac-D-Nal(2)-D-pF-Phe-D-Trp-Ser-Try-D-Deh-Leu-Deh-Pro-D-AlaNH$_2$;
N-Ac-D-Nal(2)-D-pF-Phe-D-Trp-Ser-Tyr-D-Bth-Leu-Bth-Pro-D-AlaNH$_2$;
N-Ac-D-Nal(2)-D-pF-Phe-D-Pal(3)-Ser-Tyr-D-Deh-Leu-Deh-Pro-D-AlaNH$_2$;
N-Ac-D-Nal(2)-D-pF-Phe-D-Pal(3)-Ser-Tyr-D-Bth-Leu-Bth-Pro-D-AlaNH$_2$;
N-Ac-D-Nal(2)-D-pF-Phe-D-Trp-Ser-Arg-D-Trp-Leu-Deh-Pro-D-AlaNH$_2$;
N-Ac-D-Nal(2)-D-pF-Phe-D-Trp-Ser-Arg-D-Trp-Leu-Bth-Pro-D-AlaNH$_2$;
N-Ac-D-Nal(2)-D-pF-Phe-D-Pal(3)-Ser-Arg-D-Pal(3)-Leu-Bth-Pro-D-AlaNH$_2$;
N-Ac-D-Nal(2)-D-pF-Phe-D-Pal(3)-Ser-Arg-D-Pal(3)-Leu-Deh-Pro-D-AlaNH$_2$;
N-Ac-D-Nal(2)-D-pF-Phe-D-Trp-Ser-Deh-D-Tyr-Leu-Deh-Pro-D-AlaNH$_2$; and
N-Ac-D-Nal(2)-D-pF-Phe-D-Trp-Ser-Bth-D-Tyr-Leu-Bth-Pro-D-AlaNH$_2$.

The scope of the instant invention also includes peptides that may not necessarily fall within the aforementioned preferred classes, such as:
N-Ac-D-Nal(2)-D-pCl-Phe-D-Trp-Ser-Tyr-D-Tyr-Leu-Deh-Pro-D-AlaNH$_2$;
N-Ac-D-Nal(2)-D-pCl-Phe-D-Trp-Ser-Tyr-D-Tyr-Leu-Mbh-Pro-D-AlaNH$_2$;
N-Ac-D-Nal(2)-D-pCl-Phe-D-Trp-Ser-Tyr-D-Tyr-Leu-Bth-Pro-D-AlaNH$_2$;
N-Ac-D-Nal(2)-D-pCl-Phe-D-Trp-Ser-Tyr-D-Tyr-Leu-Pha-Pro-D-AlaNH$_2$;
N-Ac-D-Nal(2)-D-pCl-Phe-D-Pal(3)-Ser-Tyr-D-Nal(2)-Leu-Deh-Pro-D-AlaNH$_2$;
N-Ac-D-Nal(2)-D-pCl-Phe-D-Pal(3)-Ser-Tyr-D-Nal(2)-Leu-Mbh-Pro-D-AlaNH$_2$;
N-Ac-D-Nal(2)-D-pCl-Phe-D-Pal(3)-Ser-Tyr-D-Nal(2)-Leu-Bth-Pro-D-AlaNH$_2$;
N-Ac-D-Nal(2)-D-pCl-Phe-D-Pal(3)-Ser-Tyr-D-Nal(2)-Leu-Pha-Pro-D-AlaNH$_2$;
N-Ac-D-Nal(2)-D-αMe,pCl-Phe-D-Pal(3)-Ser-Arg-D-Pal(3)-Leu-Bth-Pro-D-AlaNH$_2$;
N-Ac-D-Nal(2)-D-αMe,pCl-Phe-D-Pal(3)-Ser-Tyr-D-Pal(3)-Leu-Bth-Pro-D-AlaNH$_2$;
N-Ac-D-Nal(2)-D-αMe,pCl-Phe-D-Trp-Ser-Arg-D-Trp-Leu-Bth-Pro-D-AlaNH$_2$;
N-Ac-D-Nal(2)-D-pCl-Phe-D-Pal(3)-Ser-Tyr-D-Glu(AA)-Leu-Bth-Pro-D-AlaNH$_2$;
N-Ac-D-Nal(2)-D-pCl-Phe-D-Pal(3)-Ser-Arg-D-Glu(AA)-Leu-Bth-Pro-D-AlaNH$_2$;
N-Ac-D-Nal(2)-D-pCl-Phe-D-Trp-Ser-Arg-D-Glu(AA)-Leu-Bth-Pro-D-AlaNH$_2$;
N-Ac-D-pCl-Phe-D-Phe-D-Phe-Ser-Phe-D-Lys(Nic)-Nle-Bth-Pro-GlyNH$_2$;
N-Ac-Δ$^{3,4}$Pro-D-Nal(2)-D-Pal(3)-Ser-Pal(3)-D-Lys(-pyridylacetyl)-Phe-Mpa-D-AlaNH$_2$;
N-Ac-Pro-D-pNO$_2$-Phe-D-Trp-Ser-Phe-D-Lys(Nic)-Leu-Ppa-Pro-D-LeuNH$_2$;
N-Ac-D-pF-Phe-D-pF-Phe-D-Trp-Ser-Tyr-D-Tyr-Trp-Bth-Pro-AzaGlyNH$_2$;
N-Ac-D-Nal(1)-Dpg-D-Pal(3)-Ser-Tyr-D-Pal(3)-Nal(2)-Bth-Pro-D-AlaNH$_2$; and
N-Ac-D-Tmp-D-pF-Phe-D-Pal(3)-Ser-Tyr-D-Lys(-Nic)-Nal(2)-Bth-Pro-NHEt.

It is generally preferred that the A, B, C, E and J amino acid residues be in the form of the D-isomer; and that the D, F and G residues be in the form of the L-isomer. This stereochemistry is to be understood to be represented where not otherwise specified.

In all of the above embodiments, the compound may also be prepared as a corresponding pharmaceutically acceptable salt.

Assay Procedures

The compounds of this invention and, particularly, the salts thereof, exhibit surprisingly potent and long lasting LHRH antagonist activity.

A primary measure of LHRH antagonist potency is the ability to inhibit ovulation in rats, as assayed by the procedure of Corbin, A. And Beattie, C. W., *Endocrine Res. Commun.*, 2:1 (1975).

The ability to cause histamine release from rat peritoneal mast cells in vitro may be assessed as per Sydbom and Terenius, *Agents and Actions*, 16, 269 (1985) or Siraganian, et al., *Manual of Clinical Immunology*, 2d Ed, N. E. Rose and M. Friedman, Eds., Amer. Soc. Microbiol., Washington, D.C., 1980, p 808.

Other bioassays which may be used for LHRH antagonists and for the compounds of the present invention are:

(a) inhibition of LHRH induced FSH and LH release in the rat, in vivo; Vilchez-Martinez, J. A., et al, *Endocrinology*, 96: 1130 (1975); and, (b) inhibition of LH and FSH release by dispersed anterior pituitary cell cultures as measured by radioimmunoassay. (Vale, W., et al, *Endocrinology* 91: 562 (1972).

(c) inhibition of gonadotropin levels in castrated rat and dog (Petrie et al., *Male Contraception*, Harper and Row, Philadelphia (1985), p. 361).

ANTAGONIST EFFECTS AND UTILITIES

The following utilities flow from the antagonist effect of the compounds herein:
female contraception;
ovulation prevention or delay;
pregnancy termination in domestic animals and pets;
induction of parturition;
  synchronization of ovulation;
estrus suppression;
growth promotion in female animals;
luteolysis, menses induction;
therapy for premenstrual syndrome;
therapy for precocious puberty;
therapy for uterine leiomyoma;
early, first trimester abortifacient;
therapy for endometriosis;
therapy for mammary tumors and cysts
therapy for polycystic ovary syndrome/disease;
therapy for uterine carcinoma;
therapy for benign prostatic hypertrophy and for prostatic carcinoma;
male contraception;
therapy for diseases which result from excessive gonadal hormone production in either sex;
functional castration in male food producing animals;
suppression of proestrous bloody discharge in dogs;
diagnostic utilities, such as predisposition to osteoporosis;
prevention of ovarian hyperstimulation;
and other uses as set forth in Vickery, B. H., *Endocrine Reviews*, 7:115 (1986), which is fully incorporated by reference herein.

A particularly interesting use of the instant LHRH antagonists is for the prevention of ovarian hyperstimulation. Commonly, when a female subject suffers from conditions that result in a breakdown of the normal menstrual cycle, e.g., polycystic ovarian disease, menopausal syndrome resulting from chemotherapy, or oligomenorrhea, fertility can be induced either in situ or for in vitro fertilization/egg transfer, by administration of exogenous gonadotropins. However, this gonadotropic therapy often results in ovarian hyperstimulation and/or multiple births due to the combined effect of the endogenous and exogenous gonadotropins. Accordingly, the LHRH antagonists of this invention are useful to suppress endogenous gonadropins such that a normal degree of ovarian stimulation can be obtained.

The aspect of the present invention which relates to particular uses for the above-described compounds is concerned with these utilities, most particularly: inhibition of ovulation, treatment of premenstrual syndrome, treatment of ovarian hyperstimulation due to exogenous gonadotropins, and treatment of endometriosis in the female; inhibition of spermatogenesis and treatment of prostatic tumors in the male; suppression of isosexual, true (idiopathic) precocious puberty (i.e., precocious puberty of hypothalamic origin in either male or female); estrus suppression (i.e., interrupting heat in animals); and termination of pregnancy in animals.

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of controlled-release, depot implant or injectable formulations as described more fully herein below.

In general for the uses herein above described, it is expedient to administer the active ingredient in amounts between about 0.001 and 5 mg/kg body weight. Preferably, for human therapy, the active ingredient will be administered in the range of from about 0.01 to about 1 mg/kg/day; and for animal therapy, the active ingredient will be administered in the range of from about 0.1 to 1 mg/kg/day. This administration may be accomplished by a single administration, by distribution over several applications or by slow release in order to achieve the most effective results. Most preferably, for the interruption of heat or prevention of pregnancy in animals, the dose will be in the range of from about 1 to 10 mg/kg, administered as a single dose.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in *Remington's Pharmaceutical Sciences*, Mack Publishing Company, Easton, PA., 1970. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

Nasal administration of the instant nona- and decapeptides is particularly preferred. The absorption across the nasal mucous membrane is enhanced by surfactant acids, such as for example, glycocholic acid, cholic acid, taurocholic acid, cholanic acid, ethocholic acid, desoxycholic acid, chenodesoxycholic acid, dehydrocholic acid, and glycodeoxy-cholic acid.

One or more surfactant acids or salts, but preferably a single pharmaceutically acceptable acid salt, can be added to the LHRH antagonist in solution or powder formulation. Suitable pharmaceutically acceptable surfactant salts will be those salts which retain the phenomenon of enhanced peptide absorption, as well as the compound's surfactant characteristics, and which are not deleterious to the subject or otherwise contraindicated. Such salts are for example those salts derived from inorganic bases which include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

More preferably, the surfactant used in the practice of this invention will be an alkali metal salt of glycocholic acid, most preferably sodium glycocholate.

The amount of surfactant used for the practice of this invention will be some amount which increases the absorption of LHRH peptides over that of other surfactants which also may enhance peptide absorption to a certain degree. It has been found that such an amount is often in the range between 0.2 and 15%, more often 0.2 to 5 percent by weight/volume of the solution. It is preferred that the surfactant be present in an amount between about 0.5 to 4 percent by weight volume, conveniently about 1 percent by weight volume, preferably about 2 percent by weight volume.

Other materials such as preservatives, salts to achieve the tonic value of tissue, or other additives indicated by known nasal formulation chemistry may be added to these formulations. Particularly advantageous other such materials include surfactants, suitably non-ionic surfactants such as the polysorbates, in concentrations suitably in the range 0.1 to 5, more suitably 0.25 to 2% weight volume.

It has been found that often to obtain enhanced solubility and stability, the molar ratio of bile acid to peptide is usefully $\geq 20:1$, such as $\geq 25:1$.

It is particularly desirable to deliver the compounds of the present invention to the subject over prolonged periods of time, for example, for periods of one week to one year from a single administration. Various slow release, depot implant or injectable dosage forms may be utilized. For example, a dosage form may contain a pharmaceutically acceptable non-toxic salt of the compound which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection or implantation would contain the compound or salt dispersed or encapsulated in a slowly degrading, non-toxic, non-antigenic polymer such as a polylactic acid/polyglycolic acid polymer. The compounds or, preferably, relatively insoluble salts such as those described above may also be formulated in cholesterol matrix pellets, or silastomer matrix implants, particularly for use in animals. Additional slow release, depot implant or injectable formulations, e.g. liposomes, are well known in the literature. See, for example, *Sustained and Controlled Release Drug Delivery Systems*, J. R. Robinson ed., Marcel Dekker, Inc., New York, 1978. Particular reference with respect to LHRH type compounds may be found, for example, in U.S. Pat. No. 4,010,125.

SYNTHESIS OF THE PEPTIDES

The polypeptides of the present invention may be synthesized by any techniques that are known to those skilled in the peptide art. An excellent summary of the many techniques so available may be found in J. M. Stewart and J. D. Young, *Solid Phase Peptide Synthesis*, W. H. Freeman Co., San Francisco, 1969, and J. Meienhofer, *Hormonal Proteins and Peptides*, Vol. 2, p. 46., Academic Press (New York), 1973 for solid phase peptide synthesis and E. Schroder and K. Lubke, *The Peptides,* Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

PREFERRED EMBODIMENTS OF SYNTHESIS

A particularly preferred method of preparing compounds of the present invention involves solid phase peptide synthesis.

In this particularly preferred method the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups are, for arginine: nitro, p-toluenesulfonyl, 4-methoxybenzenesulfonyl, Cbz, Boc and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tetrahydropyranyl; for histidine: benzyl, p-toluenesulfonyl and 2,4-dinitrophenyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be glycinamide, a particularly useful support is the benzhydrylaminopolystyrene-divinylbenzene polymer described by P. Rivaille, et al, *Helv. Chim. Acta.,* 54, 2772 (1971). The attachment to the chloromethyl polystyrene-divinylbenzene type of resin is made by means of the reaction of the $N^\alpha$-protected amino acid, especially the Boc-amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-diisopropylcarbodiimide (DIC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichloromethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide (DIC) or other carbodiimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamino or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis. The protected peptide may be purified at this point by silica gel chromatography. The removal of the side chain protecting groups from the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about −10° and +10° C., preferably about 0° C., for between about 15 minutes and 1 hour, preferably about 30 minutes. For the glycine terminal peptides on the benzhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecylsilyl-silica bonded phase column packing.

If a racemic amino acid is used in the 1, 2, 3 or 6 position, the diastereomeric nonapeptide or decapeptide final products are separated, and the desired peptide containing a D-amino acid in the appropriate position is isolated and purified, preferably during the above-described chromatographic process.

The preparation of peptides having C-terminal azaglycine amides is preferably done using classical peptide solution synthesis using known peptide intermediates.

Thus, in another aspect the present invention relates to a method for preparing compounds of the invention and of the pharmaceutically acceptable salts thereof which process comprises:

removing protecting groups and, optionally, covalently bound solid support from a protected polypeptide to afford a compound of Formula (I) or a salt thereof, and optionally (a) converting a compound of Formula (I) to a pharmaceutically acceptable salt, or
(b) converting a salt of a compound of Formula (I) to a pharmaceutically acceptable salt, or
(c) decomposing a salt of a compound of Formula (I) to a free polypeptide of Formula (I).

The following examples are given to enable those skilled in the art to more fully understand and practice the present invention. They should not be construed as a limitation upon the scope of the invention, but merely as being illustrative and representative thereof.

PREPARATION A

3-(2-Naphthyl)-D,L-Alanine

The preparation of 3-(2-naphthyl)-D,L-alanine is carried out according to the procedure set out in U.S. Pat. No. 4,341,767.

Preparation of N-acetyl-3-(2-naphthyl)-D,L-alinine, its conversion to methyl N-acetyl-3-(2-naphthyl)-D,L-alaninate, and separation of the D isomer is carried out by the procedure disclosed in U.S. Pat. No. 4,341,767.

PREPARATION B

Benzyl N$^\alpha$-benzyloxycarbonyl-N,N'-guanidino-diisopropyl-D-homoargininate toluenesulfonate A mixture of 5.24 g of benzyl N$^\alpha$-benzyloxycarbonyl-D-lysinate toluenesulfonate (B. Bezus and L. Zervas, J. Am. Chem. Soc. 83, 719 (1961)) and 1.72 ml of diisopropylethylamine in 60 ml of dioxane is treated with 1.89 g of N,N'-diisopropylcarbodiimide. The reaction mixture is stirred at 100° C. for 6 hours, cooled to room temperature and concentrated to a solid. The solid is suspended in 20 ml of warm DMF, filtered to remove N,N'-diisopropylurea and the filtrate concentrated to a solid. Benzyl N$^\alpha$-benzyloxycarbonyl-N,N'-guanidino-diisopropyl-D-homoargininate toluenesulfonate is obtained as a white solid by crystallization from methanol/ethyl acetate $[\alpha]_D$ −7.26° (C 0.3, MeOH).

Similarly, by using the above procedure, but substituting:
N,N'-dicyclohexylcarbodiimide;
N,N'-di-n-hexylcarbodiimide;
N,N'-diethylcarbodiimide;
N,N'-di-n-propylcarbodiimide;
N-i-propylcarbodiimide;
N-propylcarbodiimide;
N-n-butylcarbodiimide;
N,N'-di-n-butylcarbodiimide;
N,N'-dimethylcarbodiimide;
N,N'-di-i-butylcarbodiimide;
N,N'-di-n-pentylcarbodiimide;
N,N'-di-i-pentylcarbodiimide;
N,N'-diphenylcarbodiimide;
N,N'-ditolylcarbodiimide; or
1-(3-dimethylaminopropyl)-3-ethylcarbodiimide-HCl;
and the like, there are obtained:
benzyl N$^\alpha$-benzyloxycarbonyl-N,N'-guanidino-dicyclohexyl-D-homoargininate, $[\alpha]_D$ 8.07° (C 0.9 MeOH);
benzyl N$^\alpha$-benzyloxycarbonyl-N,N'-guanidino-diethyl-D-homoargininate;
benzyl N$^\alpha$-benzyloxycarbonyl-N,N'-guanidino-di-n-propyl-D-homoargininate $[\alpha]_D$ 8.07° (C 0.9 MeOH);
benzyl N$^\alpha$-benzyloxycarbonyl-N-guanidino-n-propyl-D-homoargininate;
benzyl N$^\alpha$-benzyloxycarbonyl-N-guanidino-n-butyl-D-homoargininate;
benzyl N$^\alpha$-benzyloxycarbonyl-N,N'-guanidino-di-n-butyl-D-homoargininate;
benzyl N$^\alpha$-benzyloxycarbonyl-N,N'-guanidino-di-i-butyl-D-homoargininate;
benzyl N$^\alpha$-benzyloxycarbonyl-N,N'-guanidino-di-n-pentyl-D-homoargininate;
benzyl N$^\alpha$-benzyloxycarbonyl-N,N'-guanidino-di-phenyl-D-homoargininate;
benzyl N$^\alpha$-benzyloxycarbonyl-N,N'-guanidino-dimethyl-D-homoargininate;
benzyl N$^\alpha$-benzyloxycarbonyl-N,N'-guanidino-di-n-hexyl-D-homoargininate; and
benzyl N$^\alpha$-benzyloxycarbonyl-N,N'-guanidino-di-isopropyl-D-argininate, $[\alpha]_D$ −10.5° (C 0.5, MeOH); as their benzenesulfonate salts. Similarly, by substituting benzyl N$^\alpha$-benzyloxycarbonyl-D-ornithinate for the D-lysinate there may be obtained the corresponding arginine analogs as their toluenesulfonate salts.

PREPARATION C

Benzyl N$^\alpha$-benzyloxycarbonyl-N$^G$,N$^{G'}$-ethano-D-homoargininate

To a mixture of 15 ml of toluene and 15 ml of t-BuOH was added 2.71 g of benzyl N$^\alpha$-benzyloxycarbonyl-lysinate and 1.46 g of 2-methylthioimidazoline.HI (available from Aldrich). The pH of the mixture was brought to about 8 by the addition of diisopropylethylamine and the solution was heated under reflux for 24 hours.

The solution was concentrated in vacuo and the residue was loaded on a silica gel column (250 g). The column was eluted with a gradient from CH$_2$Cl$_2$/MeOH (19:1) to CH$_2$Cl$_2$/MeOH (7:3). The fractions containing product were determined by TLC, pooled, and concentrated to dryness, 2.9 g of white foam.

A 2 g portion of the above-named product was dissolved in 50 ml of EtOH containing 0.8 g of 10% Pd/C.

The solution was stirred under $H_2$ for 8 hours. The mixture was filtered on celite and the filtrate was concentrated to dryness to give $N^G,N^{G'}$-ethano-homoarginine as a white foam, 1.2 g.

In a similar manner, but employing S-methyl 3,4,5,6-tetrahydro-2-pyrimidinethiol (Aldrich) as the guanylating species, was obtained $N^G,N^{G'}$-propano-homoarginine as a white foam.

In a similar manner, but employing S-methyl bis-(2,2,2-trifluoroethyl)-thiouronium iodide as the guanylating species, there was obtained $N^G,N^{G'}$-bis(trifluoroethyl)-homoarginine (Bth) as a white foam.

PREPARATION D $N^\alpha$-t-butyloxycarbonyl-N,N'-guanidino-diisopropyl-D-homoarginine toluenesulfonate This Preparation illustrates the preparation of $N^\alpha$-t-butyloxycarbonyl derivatives of N,N'-guanidino-disubstituted-D-homoarginines from their toluenesulfonate precursors.

A mixture of benzyl $N^\alpha$-benzyloxycarbonyl-N,N'-guanidino-diisopropyl-D-homoargininate toluenesulfonate (3.25 g) and 100 mg of 10% Pd/C in 50 ml of glacial acetic acid is treated with hydrogen gas at atmospheric pressure for 4 hours. The catalyst is filtered on celite and the filtrate is concentrated to a solid, N,N'-guanidino-diisopropyl-D-homoarginine toluenesulfonate. A solution of this compound (2.13 g) in 60 ml of 50% dioxane/water is treated with 10 ml of 1N sodium hydroxide and 0.4 g of magnesium oxide. This mixture is then treated with 1.1 g of di-t-butyldicarbonate and stirred at room temperature for 2 hours. The magnesium salt is filtered and the filtrate is concentrated under vacuum. The basic solution is washed with ethanol, then brought to pH 2.5 with sodium sulfate. The acidic aqueous solution is extracted with ethylacetate which is dried over magnesium sulfate. The drying agent is filtered and the filtrate is concentrated. Crystallization from ethyl acetate/hexane affords $N^\alpha$-t-butyloxycarbonyl,N,N'-guanidino-diisopropyl-D-homoarginine toluenesulfonate.

Proceeding in a similar manner, but substituting the appropriate toluenesulfonate precursors, other $N^\alpha$-t-butyloxycarbonyl-N,N'-guanidino-disubstituted-D-homoarginine or D-arginine compounds may be prepared.

PREPARATION E $N^\alpha$-t-butyloxycarbonyl-3-(4'-(1'-propylpiperidyl))-D-alanine A 4.6 g portion of sodium metal was added to 400 ml of absolute ethanol and heated. To the resultant solution of sodium ethoxide was added 21.7 g of diethyl acetamidomalonate and 16.4 g of 4-picolyl chloride hydrochloride (Aldrich Chem. Co.). The reaction mixture was heated to 100° C. for 4 hours, cooled, filtered and concentrated in vacuo. The mixture was loaded on a silica gel column in methylene chloride/methanol (19:1) and eluted with the same mixture. The product was located as a fast running UV positive spot by TLC on silica gel in methylene chloride/methanol (19:1). Combined fractions were concentrated to provide the product.

The product from the foregoing paragraph was dissolved in 200 ml of ethanol and treated with a solution of 2.72 g of sodium hydroxide in 40 ml of water at 50° C. for 6 hours. The solution was acidified with 12 ml of 6N HCl, concentrated to dryness and taken up in 200 ml of dioxane. The suspension was filtered and the filtrate heated at reflux for 2 hours. The solution was cooled and concentrated to dryness to yield ethyl $N^\alpha$-acetyl-3-(4-pyridyl)-D,L-alanine as a white solid.

A portion of this N-acetyl ester was resolved by treatment with 200 ml of the enzyme *subtilisin Carlsberg* (Sigma Chem. Co., protease VIII) in a mixture of 300 ml of dimethyl sulfoxide and 400 ml of 0.01M KCl (pH 7.2). The pH was maintained by addition of 1N NaOH on a pH stat. After a 6 hour period, the resolution was complete. The solution was diluted with 400 ml of water and extracted with 4×750 ml of ethyl acetate. The organic layers were combined and dried over magnesium sulfate and concentrated to yield ethyl $N^\alpha$-acetyl-3-(4-pyridyl)-D-alaninate as an oil.

The oil was reacted with 1.22 g of n-propyl bromide in 50 ml of ethanol after which the solution was concentrated to dryness to yield ethyl $N^\alpha$-acetyl-3-(1-propylpyridinium-4-yl)-D-alininate bromide as a white hygroscopic solid.

This white solid was dissolved in 200 ml of ethanol and was reduced under an atmosphere of hydrogen gas using 100 mg of 10% Pd/C as a catalyst. After an 18 hour reduction period, the catalyst was filtered out and the solutin concentrated to yield ethyl $N^\alpha$-acetyl-3-(4'-(1'-propylpiperidyl))-D-alininate as a tan solid. The free acid was prepared by refluxing the ethyl ester in 100 ml of 6N HCl for 4 hours to yield 3-(4'-(1'-propylpiperidyl))-D-alanine as a white solid.

The free acid was dissolved in 100 ml of dioxane/water (1:1) and treated with 2 g of di-t-butyldicarbonate. The pH was maintained at 9 by addition of 1N NaOH on a pH stat. After 2 hours the reaction mixture was concentrated in vacuo, washed with 100 ml of ethyl ether and the aqueous layer was loaded on an Amberlite XAD-2 hydrophobic resin. The column was eluted with 250 ml of water followed by 250 ml of 50% ethanol/water. The ethanol eluate was pooled and concentrated to dryness to yield $N^\alpha$-t-butyloxycarbonyl-3-(4'-(1'-propylpiperidyl))-D-alanine as a white solid.

Proceeding in similar manner, but substituting 3-picolyl chloride hydrochloride for 4-picolyl chloride hydrochloride, there is prepared $N^\alpha$-t-butyloxycarbonyl-3-(3'-(1'-propylpiperidyl))-D-alanine.

PREPARATION F

Boc-Gly-O-Resin 4.9 g of Boc-glycine was dissolved in a mixture of 50 ml. ethanol and 50 ml. distilled water. The pH of the solution was brought to 7 with aqueous cesium bicarbonate. The solvent was then removed under vacuum.

After 18 hours of drying under high vacuum, the residue was dissolved in 150 ml. dry DMF. 25 g chloromethylated polystyrene—1% divinylbenzene (Merrifield) resin (corresponding to 25 mmole chloride) was added. The mixture was shaken at 50° C. for 24 hours, filtered, and the resin was then washed sequentially with DMF, water, and ethanol. The resin was dried under vacuum for 3 days to yield 28.34 g of Boc-Gly-O-Resin.

PREPARATION G

A. S-Methyl 3,4,5,6-tetrahydro-2-pyrimidine thio.hydroiodide

A solution of 23.24 g of 3,4,5,6-tetrahydro-2-pyrimidine thiol in 175 ml of MeOH was treated with 15.57 ml of MeI and refluxed for 1.5 hr. The solvent was evaporated under vacuum and the residue suspended in Et$_2$O. The precipitate was filtered and dried in vacuo to provide S-Methyl 3,4,5,6-tetrahydro-2-pyrimidine thiol as 51.4 g of white crystals.

B. N$^\alpha$-t-Butyloxycarbonyl-N$^G$,N$^{G'}$-propano-L-homoarginine

S-Methyl 3,4,5,6-tetrahydro-2-pyrimidine thiol was sprung from 51.4 g of its HI salt by partitioning between 300 ml of CH$_2$Cl$_2$ and 50 ml of 4N NaOH. The resulting CH$_2$Cl$_2$ solution was evaporated to ~100 ml and ~100 ml of EtOH was added. A solution of 24 g of lysine hydrochloride in 66 ml of 2N NaOH was treated at 60° C. in a dropwise fashion with the solution of S-methyl 3,4,5,6-tetrahydro-2-pyrimidine thiol. Stirring was continued overnight at 60° C. under N$_2$. An additional 10.78 g of the HI salt was sprung with 15 ml of 4N NaOH, extracted with 90% of CH$_2$Cl$_2$ and added dropwise with stirring for another 24 hour period at 60° C. at which time the reaction was essentially complete.

The reaction mixture was washed with 2 portions of EtOAc and the aqueous layer containing Pha was diluted with 200 ml of dioxane and 200 ml of H$_2$O. The solution was cooled to 0° C. before addition of 33 g of di-t-butyldicarbonate and 6 g of MgO. An additional batch of 4 g of MgO and 22 g of di-t-butyldicarbonate pushed the reaction to completion.

The MgO was filtered on celite and the filtrate was evaporated in vacuo to ½ volume. The residue was washed twice with Et$_2$O before loading on a silica gel column (750 g silica gel packed in CH$_3$CN). The column was washed with 5 L CH$_3$CN, eluted with 10% H$_2$O/CH$_3$CN (2 L), and further eluted with 20% H$_2$O/CH$_3$CN (5 L). The product fractions were located by thin layer chromatography (CN$_3$CN/HOAc/H$_2$O; 4:1:1) on silica gel plates. The product fractions were pooled and concentrated to yield the product as 5.04 g of white foam of m.p. 96° C., $[\alpha]_D^{25}$ 16.1° C. (C 0.54, MeOH), and an additional 15 g of slightly impure oil.

In a similar fashion but substituting the appropriate S-Methyl N,N'-dialkylthiouronium hydroiodides are obtained the corresponding N$^\alpha$-t-butyloxycarbonyl-N$^G$,N$^{G'}$-dialkylhomoarginines.

EXAMPLE 1

N-Ac-D-Nal(2)-D-pCl-Phe-D-Pal(3)-Ser-hArg(CH$_2$CF$_3$)$_2$-D-Tyr-Leu-hArg(CH$_2$CF$_3$)$_2$-Pro-D-Ala-NH$_2$

The title compound is also represented herein as N-Ac-D-Nal(2)-D-pCl-Phe-D-Pal(3)-Ser-Bth-D-Tyr-Leu-Bth-Pro-D-Ala-NH$_2$.

In the reaction vessel of a Beckman 990 Peptide Synthesizer was placed 0.758 g. (0.5 mmol.) of benzhydrylamino-polystyrene resin (Peninsula Labs, 0.66 mmol/g). The first amino acid was coupled by addition of 0.284 g of Boc-D-Ala-OH, 0.202 g of HBt and 3 ml of 0.5M diisopropylcarbodiimide. After a 3 hr coupling period and washing of the resin, further amino acids were added sequentially to this resin by means of a synthesis program, as follows:

| Step | | | |
|---|---|---|---|
| 1 | CH$_2$Cl$_2$ wash | 1 time | 1.5 min |
| 2 | 50% CF$_3$CO$_2$H/CH$_2$Cl$_2$—deprotection | 1 time | 1.5 min |

-continued

| Step | | | |
|---|---|---|---|
| 3 | 50% CF$_3$CO$_2$H/CH$_2$Cl$_2$—deprotection | 1 time | 30 min |
| 4 | CH$_2$Cl$_2$ wash | 3 times | 1.5 min |
| 5 | 10% triethylamine/CH$_2$Cl$_2$ | 2 times | 1.5 min |
| 6 | CH$_2$Cl$_2$ wash | 3 times | 1.5 min |
| 7 | N$^\alpha$—Boc-amino acid solution in 50% CH$_2$Cl$_2$/DMF | 1 time | add |
| 8 | N,N'—diisopropylcarbodiimide solution (0.5 M) | 1 time | add |
| 9 | CH$_2$Cl$_2$ rinse and hold-coupling | 1 time | coupling reaction 2 hr |
| 10 | CH$_2$Cl$_2$—rinse add | 1 time | 1.5 min |
| 11 | CH$_2$Cl$_2$ wash | 3 times | 1.5 min |
| 12 | ethanol wash | 3 times | 1.5 min |
| 13 | CH$_2$Cl$_2$ wash | 3 times | 1.5 min |

Steps 1-13 complete a coupling cycle for one amino acid and completeness of the reaction may be checked by the ninhydrin method of E. Kaiser, et al., *Anal. Biochem.*, 34, 595 (1970).

The resin was coupled sequentially with a 2.0 to 3.0 molar excess of each protected amino acid and DIC. Thus, the resin was treated during successive coupling cycles with 0.269 g. Boc-Pro-OH,
0.610 g. Boc-Bth-OH,
0.311 g. Boc-Leu-OH.H$_2$O
0.375 g. Boc-D-Tyr-OH,
0.610 g. Boc-Bth-OH,
0.380 g. Boc-Ser(Benzyl)-OH,
0.320 g. Boc-D-Pal(3)-OH,
0.390 g. Boc-D-pCl-Phe-OH,
0.400 g. Boc-D-Nal(2)-OH, and
2.5 ml. acetic anhydride.

The resin was removed from the reaction vessel, washed with CH$_2$Cl$_2$, and dried in vacuo to yield 1.43 g. of protected polypeptide resin. The protected peptide was deprotected and removed from the resin by treatment with 25 ml. anhydrous liquid HF in the presence of 2.5 ml. of anisole (scavenger) in a Kel-F reaction vessel at 0° C. for 1 hr. The HF was evaporated under vacuum and the residue of N-Ac-D-Nal(2)-D-pCl-Phe-D-Pal(3)-Ser-hArg(CH$_2$CF$_3$)$_2$-D-Tyr-Leu-hArg(CH$_2$CF$_3$)$_2$-Pro-D-Ala-NH$_2$, as its HF salt, was washed with ether. The residue was then extracted with glacial acetic acid (3×30 ml). The acetic acid extract was evaporated to dryness. The crude material was converted to the acetate salt by passage in water through a column of AG3 (a weakly basic tertiary amine resin) which had been converted to the acetate form. Lyophilization of the eluate yielded 0.5 g. of the crude peptide acetate salt as a white solid.

The crude peptide was purified by high performance liquid chromatography on a 2.5×100 cm. column of Licroprep RP-18 (25-40 micron) equilibrated to the running buffer 50% CH$_3$CN/50% H$_2$O (0.1% in CF$_3$CO$_2$H, pH 2.5). The major UV absorbing (280 nm) peak eluting at approximately 2 column volumes was collected, concentrated to dryness, and lyophilized 3 times from distilled water to yield 64 mg of pure N-Ac-D-Nal(2)-D-pCl-Phe-D-Pal(3)-Ser-hArg(CH$_2$CF$_3$)$_2$-D-Tyr-Leu-hArg(CH$_2$CF$_3$)$_2$-Pro-D-Ala-NH$_2$, $[\alpha]_D^{25}$=−17.96° (C 0.4, HOAc).

B. Proceeding in a similar manner but substituting the appropriate A, B, C, D, E, F, G or J amino acid for those recited, there were prepared the corresponding decapeptides exemplified below:

N-Ac-D-Nal(2)-D-pCl-Phe-D-Pal(3)-Ser-Tyr-D-Pal(3)-Leu-Deh-Pro-D-AlaNH$_2$;
N-Ac-D-Nal(2)-D-pCl-Phe-D-Pal(3)-Ser-Mbh-D-Pal(3)-Leu-Mbh-Pro-D-AlaNH$_2$;
N-Ac-D-Nal(2)-D-pCl-Phe-D-Pal(3)-Ser-Pal(3)-D-Pal(3)-Leu-Bth-Pro-D-AlaNH$_2$;
N-Ac-D-Nal(2)-D-pCl-Phe-D-Pal(3)-Ser-Arg-D-Pal(3)-Leu-Deh-Pro-D-AlaNH$_2$;
N-Ac-D-Nal(2-D-pCl-Phe-D-Pal(3)-Ser-Tyr-D-Pal(3)-Leu-Bth-Pro-D-AlaNH$_2$;
N-Ac-D-Nal(2)-D-pCl-Phe-D-Pal(3)-Ser-Tyr-D-Pal(3)-Leu-Mbh-Pro-D-AlaNH$_2$;
N-Ac-D-Nal(2)-D-pCl-Phe-D-Pal(3)-Ser-Tyr-D-Pal(3)-Leu-Pha-Pro-D-AlaNH$_2$;
N-Ac-D-Nal(2)-D-pCl-Phe-D-Trp-Ser-Tyr-D-Trp-Leu-Bth-Pro-D-AlaNH$_2$;
N-Ac-D-Nal(2)-D-pCl-Phe-D-Trp-Ser-Arg-D-Trp-Leu-Deh-Pro-D-AlaNH$_2$;
N-Ac-D-Nal(2)-D-pCl-Phe-D-Trp-Ser-Arg-D-Trp-Leu-Bth-Pro-D-AlaNH$_2$;
N-Ac-D-Nal(2)-D-pCl-Phe-D-Trp-Ser-Arg-D-Trp-Leu-Pha-Pro-D-AlaNH$_2$;
N-Ac-D-Nal(2)-D-pCl-Phe-D-Pal(3)-Ser-Arg-D-Pal(3)-Leu-Pha-Pro-D-AlaNH$_2$;
N-Ac-D-Nal(2)-D-pCl-Phe-D-Trp-Ser-Tyr-D-Bth-Leu-Bth-Pro-D-AlaNH$_2$;
N-Ac-D-Nal(2)-D-pCl-Phe-D-Trp-Ser-Tyr-D-Pha-Leu-Pha-Pro-D-AlaNH$_2$;
N-Ac-D-Nal(2)-D-pCl-Phe-D-Pal(3)-Ser-Tyr-D-Deh-Leu-Deh-Pro-D-AlaNH$_2$; and
N-Ac-D-Nal(2)-D-pCl-Phe-D-Pal(3)-Ser-Tyr-D-Bth-Leu-Bth-Pro-D-AlaNH$_2$.

C. Proceeding in a similar manner but substituting the appropriate A, B, C, D, E, F, G or J amino acid for those recited, there are prepared the corresponding decapeptides exemplified below:

N-Ac-D-Nal(2)-D-pCl-Phe-D-Trp-Ser-Tyr-D-Trp-Leu-Deh-Pro-D-AlaNH$_2$;
N-Ac-D-Nal(2)-D-pCl-Phe-D-Trp-Ser-Tyr-D-Trp-Leu-Mbh-Pro-D-AlaNH$_2$;
N-Ac-D-Nal(2)-D-pCl-Phe-D-Trp-Ser-Tyr-D-Trp-Leu-Pha-Pro-D-AlaNH$_2$;
N-Ac-D-Nal(2)-D-pCl-Phe-D-Trp-Ser-Tyr-D-Deh-Leu-Deh-Pro-D-AlaNH$_2$;
N-Ac-D-Nal(2)-D-pCl-Phe-D-Trp-Ser-Tyr-D-Mbh-Leu-Mbh-Pro-D-AlaNH$_2$;
N-Ac-D-Nal(2)-D-pCl-Phe-D-Pal(3)-Ser-Tyr-D-Mbh-Leu-Mbh-Pro-D-AlaNH$_2$;
N-Ac-D-Nal(2)-D-pCl-Phe-D-Pal(3)-Ser-Tyr-D-Pha-Leu-Pha-Pro-D-AlaNH$_2$;
N-Ac-D-Nal(2)-D-pCl-Phe-D-Trp-Ser-Arg-D-Trp-Leu-Mbh-Pro-D-AlaNH$_2$;
N-Ac-D-Nal(2)-D-pCl-Phe-D-Pal(3)-Ser-Arg-D-Pal(3)-Leu-Bth-Pro-D-AlaNH$_2$;
N-Ac-D-Nal(2)-D-pCl-Phe-D-Pal(3)-Ser-Arg-D-Pal(3)-Leu-Mbh-Pro-D-AlaNH$_2$;
N-Ac-D-Nal(2)-D-pCl-Phe-D-Trp-Ser-Arg-D-Tyr-Leu-Deh-Pro-D-AlaNH$_2$;
N-Ac-D-Nal(2)-D-pCl-Phe-D-Trp-Ser-Arg-D-Tyr-Leu-Bth-Pro-D-AlaNH$_2$;
N-Ac-D-Nal(2)-D-pCl-Phe-D-Trp-Ser-Arg-D-Tyr-Leu-Mbh-Pro-D-AlaNH$_2$;
N-Ac-D-Nal(2)-D-pCl-Phe-D-Trp-Ser-Arg-D-Tyr-Leu-Pha-Pro-D-AlaNH$_2$;
N-Ac-D-Nal(2)-D-pCl-Phe-D-Pal(3)-Ser-Arg-D-Tyr-Leu-Bth-Pro-D-AlaNH$_2$;
N-Ac-D-Nal(2)-D-pCl-Phe-D-Pal(3)-Ser-Arg-D-Tyr-Leu-Mbh-Pro-D-AlaNH$_2$;
N-Ac-D-Nal(2)-D-pCl-Phe-D-Pal(3)-Ser-Arg-D-Tyr-Leu-Deh-Pro-D-AlaNH$_2$;
N-Ac-D-Nal(2)-D-pCl-Phe-D-Pal(3)-Ser-Arg-D-Tyr-Leu-Pha-Pro-D-AlaNH$_2$;
N-Ac-D-Nal(2)-D-pCl-Phe-D-Trp-Ser-Deh-D-Tyr-Leu-Deh-Pro-D-AlaNH$_2$;
N-Ac-D-Nal(2)-D-pCl-Phe-D-Trp-Ser-Mbh-D-Tyr-Leu-Mbh-Pro-D-AlaNH$_2$;
N-Ac-D-Nal(2)-D-pCl-Phe-D-Trp-Ser-Bth-D-Tyr-Leu-Bth-Pro-D-AlaNH$_2$;
N-Ac-D-Nal(2)-D-pCl-Phe-D-Trp-Ser-Pha-D-Tyr-Leu-Pha-Pro-D-AlaNH$_2$;
N-Ac-D-Nal(2)-D-pCl-Phe-D-Trp-Ser-Deh-D-Trp-Leu-Deh-Pro-D-AlaNH$_2$;
N-Ac-D-Nal(2)-D-pCl-Phe-D-Trp-Ser-Mbh-D-Trp-Leu-Mbh-Pro-D-AlaNH$_2$;
N-Ac-D-Nal(2)-D-pCl-Phe-D-Trp-Ser-Bth-D-Trp-Leu-Bth-Pro-D-AlaNH$_2$;
N-Ac-D-Nal(2)-D-pCl-Phe-D-Trp-Ser-Pha-D-Trp-Leu-Pha-Pro-D-AlaNH$_2$;
N-Ac-D-Nal(2)-D-pCl-Phe-D-Pal(3)-Ser-Deh-D-Pal(3)-Leu-Deh-Pro-D-AlaNH$_2$;
N-Ac-D-Nal(2)-D-pCl-Phe-D-Pal(3)-Ser-Mbh-D-Pal(3)-Leu-Mbh-Pro-D-AlaNH$_2$;
N-Ac-D-Nal(2)-D-pCl-Phe-D-Pal(3)-Ser-Bth-D-Pal(3)-Leu-Bth-Pro-D-AlaNH$_2$;
N-Ac-D-Nal(2)-D-pCl-Phe-D-Pal(3)-Ser-Pha-D-Pal(3)-Leu-Pha-Pro-D-AlaNH$_2$;
N-Ac-D-Nal(2)-D-pCl-Phe-D-Trp-Ser-Deh-D-Nal(2)-Leu-Deh-Pro-D-AlaNH$_2$;
N-Ac-D-Nal(2)-D-pCl-Phe-D-Trp-Ser-Mbh-D-Nal(2)-Leu-Mbh-Pro-D-AlaNH$_2$;
N-Ac-D-Nal(2)-D-pCl-Phe-D-Trp-Ser-Bth-D-Nal(2)-Leu-Bth-Pro-D-AlaNH$_2$;
N-Ac-D-Nal(2)-D-pCl-Phe-D-Trp-Ser-Pha-D-Nal(2)-Leu-Pha-Pro-D-AlaNH$_2$;
N-Ac-D-Nal(2)-D-pCl-Phe-D-Pal(3)-Ser-Pal(3)-D-Pal(3)-Leu-Deh-Pro-D-AlaNH$_2$;
N-Ac-D-Nal(2)-D-pCl-Phe-D-Pal(3)-Ser-Pal(3)-D-Pal(3)-Leu-Bth-Pro-D-AlaNH$_2$;
N-Ac-D-Nal(2)-D-pCl-Phe-D-Pal(3)-Ser-Pal(3)-D-Pal(3)-Leu-Pha-Pro-D-AlaNH$_2$; and
N-Ac-D-Nal(2)-D-pCl-Phe-D-Pal(3)-Ser-Pal(3)-D-Pal(3)-Leu-Mbh-Pro-D-AlaNH$_2$.

EXAMPLE 2

N-Ac-D-Nal(2)-D-pCl-Phe-D-Pal(3)-Ser-hArg(CH$_2$CF$_3$)$_2$-D-Tyr-Leu-hArg(CH$_2$CF$_3$)$_2$-Pro-NHEt

For the synthesis of analogs with a C-terminal Pro-NHCH$_2$CH$_3$, a synthesis program identical to that described in Example 1 is used. The Beckman 990 Synthesizer reaction vessel is loaded with 0.71 g. of Boc-Pro-O-Resin, prepared by the reaction of 1.3 molar excess of the dry cesium salt of Boc-Pro-OH with chloromethyl-polystyrene/1% divinylbenzene (Lab Systems, Inc.). The quantity of Boc-Pro-O-Resin taken contains 0.5 mmol. of proline.

The resin is coupled sequentially with a 2.0 to 3.0 molar excess of each protected amino acid and DIC. Thus, the resin is reacted during successive coupling cycles with
0.610 g. Boc-Bth-OH,
0.311 g. Boc-Leu-OH.H$_2$O
0.375 g. Boc-D-Tyr-OH, 0.610 g. Boc-Bth-OH,
0.380 g. Boc-Ser(Benzyl)-OH,
0.320 g. Boc-D-Pal(3)-OH,
0.390 g. Boc-D-pCl-Phe-OH,
0.400 g. Boc-D-Nal(2)-OH, and
2.5 ml. acetic anhydride.

The resin is removed from the reaction vessel, washed with $CH_2Cl_2$, and dried in vacuo to yield 1.5 g. of protected polypeptide resin.

The protected polypeptide is cleaved from the resin by aminolysis with 25 ml. of ethylamine for 18 hours at 2° C. The ethylamine is allowed to evaporate and the resin is extracted with methanol. The methanol is evaporated to yield 0.7 g. of protected peptide. This protected peptide is mixed with 2.5 ml of anisole and 25 ml of redistilled (from $CoF_3$) anhydrous liquid HF at 0° C. for 1 hour in a Kel-F reaction vessel. The HF is evaporated under vacuum and the residue is washed with ether. The residue is dissolved in 2M acetic acid and converted to the acetate salt by passage in water through a column of AG3 which had been converted to the acetate form. Lyophilization of the eluate yields 0.5 g. of the crude peptide acetate salt as a white solid. Final purification is achieved by preparative high performance liquid chromatography on a 2.5×100 mm. column of 40–50 micron octadecylsilylated silica (Merck, Lichroprep $C_{18}$) using 50% $CH_3CH$ (0.1% $CF_3CO_2H$) as eluate. Lypophilization of the product from $H_2O$ yields N-Ac-D-Nal(2)-D-pCl-Phe-D-Pal(3)-Ser-hArg($CH_2CF_3$)$_2$-D-Tyr-Leu-hArg($CH_2CF_3$)$_2$-ProN-HEt as 70 mg of white powder.

Proceeding in a similar manner, but substituting the required protected amino acid residues where appropriate, there are prepared the following compounds:

N-Ac-D-Nal(2)-D-pCl-Phe-D-Pal(3)-Ser-Tyr-D-Pal(3)-Leu-Bth-Pro-NHEt,

N-Ac-D-Nal(2)-D-pCl-Phe-D-Pal(3)-Ser-Tyr-D-Pal(3)-Leu-Mbh-Pro-NHEt,

N-Ac-D-Nal(2)-D-pCl-Phe-D-Pal(3)-Ser-Tyr-D-Pal(3)-Leu-Pha-Pro-NHEt,

N-Ac-D-Nal(2)-D-pCl-Phe-D-Pal(3)-Ser-Tyr-D-Pal(3)-Leu-Deh-Pro-NHEt,

N-Ac-D-Nal(2)-D-pCl-Phe-D-Trp-Ser-Arg-D-Nal(2)-Leu-Bth-Pro-NHEt.

Repeating the above cleavage, substituting a stoichiometric amount of methylamine and propylamine for ethylamine there are obtained the corresponding methylamides or propylamides of the aforementioned nonapeptides.

EXAMPLE 3

Preparation of Salts

A. A solution of 0.1 g of the hydrogen fluoride salt of (N-Ac-D-Nal(2)[1], D-pCl-Phe[2], D-Pal(3)[3,6], Bth[8], D-Ala[10])LHRH (See Example 1) is dissolved in 50 ml of water and passed through a column of 50 g Dowex 3 anion exchange resin which had previously been equilibrated with acetic acid and washed with deionized water. The column is eluted with deionized water and the effluent is lyophilized to yield the corresponding acetic acid salt of (N-Ac-D-Nal(2)[1], D-pCl-Phe[2], D-Pal(3)[3,6], Bth[8], D-Ala[10])LHRH.

Repeating the above, substituting other acids for acetic acid during the equilibration of the resin, there may be obtained, for example, the corresponding salts with hydrochloric acid, hydrobromic acid, sulfuric acid, phosphoric acid, nitric acid, benzoic acid, and the like.

Similarly there may be prepared the acid addition salts of the other peptides analogous to LHRH, described herein.

B. In the case of salts of low water solubility, these may be prepared by precipitation from water utilizing the desired acid. For example:

Zinc tannate salt—a solution of 10 mg of (N-Ac-D-Nal(2)[1], D-pCl-Phe[2], D-Pal(3)[3,6], Bth[8], D-Ala[10])LHRH acetic acid salt in 0.1 ml of water was treated with a solution of 8 mg of tannic acid in 0.08 ml of 0.25M NaOH. A solution of 5 mg of $ZnSO_4$ heptahydrate in 0.1 ml of water was immediately added to the solution of the LHRH analog.

The resultant suspension was diluted with 1 ml water and the precipitate was centrifuged. The supernatant was decanted and the residue was washed twice with 1 ml portions of water by centrifugation of the precipitate and decantation of the supernatant. The precipitate was dried in vacuo to yield 15 mg of the mixed zinc tannate salt of the above named LHRH analog.

Pamoate salt—to a solution of 50 mg (N-Ac-D-Nal(2)[1], D-pCl-Phe[2], D-Pal(3)[3,6], Bth[8], D-Ala[10])LHRH acetic acid salt in a mixture of 1.6 ml of ethanol and 0.1 ml of 0.25M NaOH was added a solution of 11 mg of pamoic acid in 0.3 ml of 0.25M NaOH. The solvents were removed at reduced pressure and the residue was suspended in 2 ml of water, centrifuged, and the supernatant was decanted. The precipitate was washed with 1.5 ml $H_2O$, centrifuged, and the supernatant was decanted. The precipitate was dried in vacuo to yield 54 mg of the pamoate salt of the above named LHRH analog.

In a similar manner other salts of low water solubility may be prepared.

C. Preparation of acid addition salt from free peptide.

To a solution of 50 mg of (N-Ac-D-Nal(2)[1], D-pCl-Phe[2], D-Pal(3)[3,6], Bth[8], D-Ala[10])LHRH as the free base is added 30 ml of 1N acetic acid. The resulting solution is lyophilized to yield 50 mg of the acetic acid salt of the above.

Similarly, replacing acetic acid with other acids (in stoichiometrically equivalent amounts relative to peptide) there are obtained other acid addition salts of the peptides herein, for example, the salts with hydrochloric acid, hydrobromic acid, sulfuric acid, phosphoric acid, nitric acid.

D. Preparation of salt with metal cation, e.g., zinc salt.

To a solution of 50 mg (N-Ac-D-Nal(2)[1], D-pCl-Phe[2], D-Pal(3)[3,6], Bth[8], D-Ala-[10])LHRH acetic acid salt in a mixture of 0.4 ml of 0.25M NaOH, 0.3 ml water, and 1 ml ethanol was added a solution of 15 mg of $ZnSO_4$ heptahydrate in 0.2 ml of water. The precipitate was centrifuged and the supernatant was decanted. The precipitate was washed with 1 ml of water by centrifugation and decantation of the supernatant. The precipitate was dried in vacuo to yield the zinc salt of the above named LHRH analog.

In a similar manner salts with other multivalent cations e.g. calcium, bismuth, barium, magnesium, aluminum, copper, cobalt, nickel, cadmium and the like, may be prepared.

EXAMPLE 4

Conversion of Salts to Free Base

A solution of 50 mg of (N-Ac-D-Nal(2)$^1$, D-pCl-Phe$^2$, D-Pal(3)$^{3,6}$, Bth$^8$, D-Ala$^{10}$)LHRH acetic acid salt in 25 ml. of water is passed through a 50 g column of Dowex 1 (strongly basic, quaternary ammonium anion exchange resin) which had been equilibrated with NaOH solution to make the counter ion hydroxide. The column is eluted with 150 ml of water and the eluant is lyophilized to yield 45 mg of the corresponding polypeptide as the free base.

Similarly other acid addition salts of compounds of the peptides herein, e.g., those mentioned in Example 6, may be converted to the corresponding free bases.

EXAMPLE 5

Pharmaceutical Formulations

The following are typical pharmaceutical compositions containing, as active ingredient, an LHRH antagonist of the present invention, for example (N-Ac-D-Nal(2)$^1$, D-pCl-Phe$^2$, D-Pal(3)$^{3,6}$, Bth$^8$, D-Ala$^{10}$)LHRH, by itself or as a pharmaceutically acceptable salt, e.g., the acetic acid addition salt, the zinc salt, the zinc tannate salt, etc.

| A. Tablet Formulations | | |
|---|---|---|
| 1. | LHRH Antagonist | 10.0 mg |
|  | Compressible Sugar, USP | 86.0 mg |
|  | Calcium Stearate | 4.0 mg |
| 2. | LHRH Antagonist | 10.0 mg |
|  | Compressible Sugar, USP | 88.5 mg |
|  | Magnesium Stearate | 1.5 mg |
| 3. | LHRH Antagonist | 5.0 mg |
|  | Mannitol, USP | 83.5 mg |
|  | Magnesium Stearate, USP | 1.5 mg |
|  | Pregelatinized Starch, USP | 10.0 mg |
| 4. | LHRH Antagonist | 10.0 mg |
|  | Lactose, USP | 74.5 mg |
|  | Pregelatinized Starch, USP | 15.0 mg |
|  | Magnesium Stearate, USP | 1.5 mg |

METHOD OF MANUFACTURE (a) LHRH Antagonist is dissolved in water, a sufficient quantity to form a wet granulation when mixed with the sugar portion of the excipients. After complete mixing, the granulation is dried in a tray or fluid-bed dryer. The dry granulation is then screened to break up any large aggregates and then mixed with the remaining components. The granulation is then compressed on a standard tabletting machine to the specific tablet weight.

(b) In this manufacturing method, all formulations would include 0.01% gelatin, USP. The gelatin would be first dissolved in the aqueous granulation solvent followed by the LHRH analog. The remaining steps are as in (a) above.

Formulation 4 could also be used as a tablet for oral administration.

| B. Long Acting Intramuscular Injectable Formulation | |
|---|---|
| 1. Long Acting I.M. Injectable - Sesame Oil Gel | |
| LHRH Antagonist | 10.0 mg |
| Aluminum monostearate, USP | 20.0 mg |
| Sesame oil q.s. ad | 1.0 ml |

The aluminum monostearate is combined with the sesame oil and heated to 125° C. with stirring until a clear yellow solution forms. This mixture is then autoclaved for sterility and allowed to cool. The LHRH analog is then added aseptically with trituration. Particularly preferred LHRH analogs are salts of low solubility, e.g. zinc salts, zinc tannate salts, pamoate salts, and the like. These exhibit exceptionally long duration of activity.

| 2. Long Acting I.M. Injectable - Biodegradable Polymer Microcapsules | |
|---|---|
| LHRH Antagonist | 7% |
| 25/75 glycolide/lactide copolymer (0.5 intrinsic viscosity) | 93% |

Microcapsules of above formulation suspended in:

| | |
|---|---|
| Dextrose | 5.0% |
| CMC, sodium | 0.5% |
| Benzyl alcohol | 0.9% |
| Tween 80 | 0.1% |
| Water, purified q.s. | 100.0% |

25 mg of microcapsules would be suspended in 1.0 ml of vehicle.

| C. Aqueous Solution for Intramuscular Injection | |
|---|---|
| LHRH Antagonist | 0.5% |
| Acetic Acid | 0.02 M |
| Benzyl Alcohol | 0.9% |
| Mannitol | 3.5% |
| Propylene Glycol | 20% |
| NaOH sufficient to adjust pH to | 5 |
| Water q.s. to | 100% |

Acetic acid, benzyl alcohol, mannitol and propylene glycol were dissolved in 90% of the water. Then the Antagonist was dissolved in this solution, and the pH adjusted with NaOH. Water was added to q.s. The solution was filtered through a one micron filter, packaged into vials, and sterilized by autoclaving.

| D. Aqueous Formulation for Nasal Administration | |
|---|---|
| LHRH Antagonist | 50 mg |
| 0.02 M Acetate Buffer | 5 ml |
| Sodium Glycocholate | 500 mg |
| 0.02 Acetate Buffer, pH 5.2 q.s. | 10 ml |
| E. Formulation for Rectal Administration | |
| Suppository Vehicle: | |
| LHRH Antagonist | 5.0 mg |
| Witepsol H15 | 20.0 gm |

The LHRH antagonist is combined with the molten Witepsol H15, mixed well and poured into 2 gm molds.

What is claimed is:

1. A compound of the formula

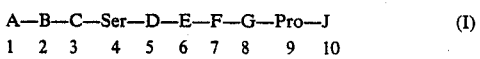

or a pharmaceutically acceptable salt thereof, wherein:
A is an amino acyl residue selected from the group consisting of either the D- or the L-isomer of: N-Ac-D,L-Δ$^{3,4}$-prolyl, N-Ac-D,L-prolyl, N-Ac-D,L-phenylalanyl, N-Ac-D,L-p-chlorophenylalanyl, N-

Ac-D,L,-p-fluorophenylalanyl, N-Ac-3-(1-naphthyl)-D,L-alanyl, N-Ac-3-(2-naphthyl)-D,L-alanyl, and N-Ac-3-(2,4,6-trimethylphenyl)-D,L-alanyl;

B is an amino acyl residue selected from the group consisting of D-phenylalanyl, D-p-chlorophenylalanyl, D-p-fluorophenylalanyl, D-p-nitrophenylalanyl, 2,2-diphenylglycyl, D-α-methyl-p-chlorophenylalanyl and 3-(2-naphthyl)-D-alanyl;

C is an amino acyl residue selected from the group consisting of D-tryptophanyl, D-phenylalanyl, 3-(3-pyridyl)-D-alanyl, and 3-(2-naphthyl)-D-alanyl;

D is an amino acyl residue selected from the group consisting of L-phenylalanyl, L-tyrosyl, and 3-(3-pyridyl)-alanyl, arginyl, or G;

E is 3-(2-naphthyl)-D-alanyl, 3-(3-pyridyl)-D-alanyl, D-tyrosyl, D-tryptophanyl, D-nicotinyl-lysyl, pyridylacetyl-lysyl, D-Glu(AA) or G;

F is an amino acyl residue selected from the group consisting of L-leucyl, L-norleucyl, L-phenylalanyl, L-tryptophanyl, and 3-(2-naphthyl)-L-alanyl;

G is an amino acyl residue selected from the group consisting of the radicals represented by the following structural formulas:

(a)
$$-HN-CH-CO- \quad (II)$$
$$|$$
$$(CH_2)_n$$
$$|$$
$$NH$$
$$|$$
$$R^1-HN-C=NR^2$$

wherein
n is 1 to 5;
$R^1$ is alkyl of 1 to 6 carbon atoms or fluoroalkyl;
$R^2$ is hydrogen or $R^1$; or $R^1-HN-C=NR^2$ is a ring represented by the following structure formulas:

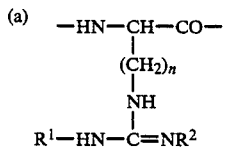

wherein m is 1 to 4; A is hydrogen or alkyl of 1 to 6 carbon atoms; and X is halo or A; and (b)
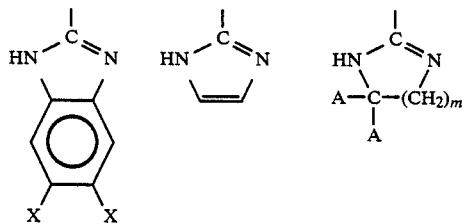

wherein
$R^3$ is hydrogen, alkyl of 1 to 6 carbon atoms, phenyl or phenylloweralkyl; and
J is D-alaninamide; D-leucinamide; glycinamide; or $-NHR^4$ wherein $R^4$ is lower alkyl or $NHCONH_2$.

2. A compound of claim 2 wherein:
A is N-Ac-D-Nal(2) or N-Ac-D-pCl-Phe;
B is D-pCl-Phe or D-pF-Phe;
C is D-Trp, D-Nal(2) or D-Pal(3);
D is Pal(3), Tyr, Arg, Deh, Mbh, Bth or Pha;
E is D-Trp, D-Tyr, D-Nal(2), D-Pal(3), D-Deh, D-Bth, D-Mbh or D-Pha;
F is Leu or Phe;
G is Deh, Bth, Mbh, or Pha; and
J is D-AlaNH$_2$ or GlyNH$_2$;
or a pharmaceutically acceptable salt thereof.

3. A compound of claim 2 wherein:
A is N-Ac-D-Nal(2);
B is D-pCl-Phe;
C is D-Trp or D-Pal(3);
D is Tyr, Arg, Deh, Mbh, Bth or Pha;
F is Leu; and
J is D-AlaNH$_2$;
or a pharmaceutically acceptable salt thereof.

4. A compound of claim 3 wherein G is Deh or Bth or a pharmaceutically acceptable salt thereof.

5. A compound of claim 4 wherein G is Bth or a pharmaceutically acceptable salt thereof.

6. A compound of claim 3 which is
N-Ac-D-Nal(2)-D-pCl-Phe-C-Ser-Tyr-E-Leu-G-Pro-D-AlaNH$_2$ wherein E is D-Pal(3) or D-Trp;
or a pharmaceutically acceptable salt thereof.

7. A compound of claim 6 wherein C and E are the same or a pharmaceutically acceptable salt thereof.

8. A compound of claim 3 which is
N-Ac-D-Nal(2)-D-pCl-Phe-C-Ser-Tyr-E-Leu-G-Pro-D-AlaNH$_2$, wherein E is D-Deh, D-Bth, D-Mbh or D-Pha;
or a pharmaceutically acceptable salt thereof.

9. A compound of claim 3 which is
N-Ac-D-Nal(2)-D-pCl-Phe-C-Ser-Arg-E-Leu-G-Pro-D-AlaNH$_2$, wherein E is D-Trp, D-Pal(3), D-Nal(2), or D-Tyr;
or a pharmaceutically acceptable salt thereof.

10. A compound of claim 9 wherein E is D-Tyr;
or a pharmaceutically acceptable salt thereof.

11. A compound of claim 9 wherein E is D-Trp or D-Pal(3);
or a pharmaceutically acceptable salt thereof.

12. A compound of claim 11 wherein C and E are the same;
or a pharmaceutically acceptable salt thereof.

13. A compound of claim 3 which is
N-Ac-D-Nal(2)-D-pCl-Phe-C-Ser-D-E-Leu-G-Pro-D-AlaNH$_2$, wherein D is Deh, Bth, Mbh or Pha, and E is D-Tyr, D-Nal(2), D-Trp or D-Pal(3);
or a pharmaceutically acceptable salt thereof.

14. A compound of claim 13 wherein E is D-Tyr or D-Pal(3) or a pharmaceutically acceptable salt thereof.

15. A compound of claim 3 which is N-Ac-D-Nal(2)-D-pCl-Phe-D-Trp-Ser-Tyr-E-Leu-G-Pro-D-AlaNH$_2$, wherein E is D-Trp, D-Tyr, or D-Nal(2);
or a pharmaceutically acceptable salt thereof.

16. A compound of claim 3 which is
N-Ac-D-Nal(2)-D-pCl-Phe-C-Ser-D-E-Leu-G-Pro-D-AlaNH$_2$, wherein D and G are independently Deh, Bth, Mbh or Pha, and C and E are independently D-Trp or D-Pal(3);
or a pharmaceutically acceptable salt thereof.

17. A compound of claim 3 which is
N-Ac-D-Nal(2)-D-pCl-Phe-D-Pal(3)-Ser-Tyr-D-Pal(3)-Leu-G-Pro-D-AlaNH$_2$;
or a pharmaceutically acceptable salt thereof.

18. A compound of claim 3 selected from the group consisting of:

N-Ac-D-Nal(2)-D-pCl-Phe-D-Pal(3)-Ser-Tyr-D-Pal(3)-Leu-Deh-Pro-D-AlaNH₂;

N-Ac-D-Nal(2)-D-pCl-Phe-D-Pal(3)-Ser-Tyr-D-Pal(3)-Leu-Bth-Pro-D-AlaNH₂;

N-Ac-D-Nal(2)-D-pCl-Phe-D-Pal(3)-Ser-Tyr-D-Pal(3)-Leu-Mbh-Pro-D-AlaNH₂;

N-Ac-D-Nal(2)-D-pCl-Phe-D-Pal(3)-Ser-Tyr-D-Pal(3)-Leu-Pha-Pro-D-AlaNH₂;

N-Ac-D-Nal(2)-D-pCl-Phe-D-Trp-Ser-Tyr-D-Trp-Leu-Deh-Pro-D-AlaNH₂;

N-Ac-D-Nal(2)-D-pCL-Phe-D-Trp-Ser-Tyr-D-Trp-Leu-Bth-Pro-D-AlaNH₂;

N-Ac-D-Nal(2)-D-pCl-Phe-D-Trp-Ser-Tyr-D-Trp-Leu-Mbh-Pro-D-AlaNH₂; and

N-Ac-D-Nal(2)-D-pCl-Phe-D-Trp-Ser-Tyr-D-Trp-Leu-Pha-Pro-D-AlaNH₂;

or a pharmaceutically acceptable salt thereof.

19. A compound of claim 3 selected from the group consisting of:

N-Ac-D-Nal(2)-D-pCl-Phe-D-Trp-Ser-Tyr-D-Deh-Leu-Deh-Pro-D-AlaNH₂;

N-Ac-D-Nal(2)-D-pCl-Phe-D-Trp-Ser-Tyr-D-Mbh-Leu-Mbh-Pro-D-AlaNH₂;

N-Ac-D-Nal(2)-D-pCl-Phe-D-Trp-Ser-Tyr-D-Bth-Leu-Bth-Pro-D-AlaNH₂;

N-Ac-D-Nal(2)-D-pCL-Phe-D-Trp-Ser-Tyr-D-Pha-Leu-Pha-Pro-D-AlaNH₂;

N-Ac-D-Nal(2)-D-pCl-Phe-D-Pal(3)-Ser-Tyr-D-Deh-Leu-Deh-Pro-D-AlaNH₂;

N-Ac-D-Nal(2)-D-pCl-Phe-D-Pal(3)-Ser-Tyr-D-Mbh-Leu-Mbh-Pro-D-AlaNH₂;

N-Ac-D-Nal(2)-D-pCl-Phe-D-Pal(3)-Ser-Tyr-D-Bth-Leu-Bth-Pro-D-AlaNH₂; and

N-Ac-D-Nal(2)-D-pCl-Phe-D-Pal(3)-Ser-Tyr-D-Pha-Leu-Pha-Pro-D-AlaNH₂;

or a pharmaceutically acceptable salt thereof.

20. A compound of claim 3 selected from the group consisting of:

N-Ac-D-Nal(2)-D-pCl-Phe-D-Trp-Ser-Arg-D-Trp-Leu-Deh-Pro-D-AlaNH₂;

N-Ac-D-Nal(2)-D-pCl-Phe-D-Trp-Ser-Arg-D-Trp-Leu-Bth-Pro-D-AlaNH₂;

N-Ac-D-Nal(2)-D-pCl-Phe-D-Trp-Ser-Arg-D-Trp-Leu-Mbh-Pro-D-AlaNH₂;

N-Ac-D-Nal(2)-D-pCl-Phe-D-Trp-Ser-Arg-D-Trp-Leu-Pha-Pro-D-AlaNH₂;

N-Ac-D-Nal(2)-D-pCl-Phe-D-Pal(3)-Ser-Arg-D-Pal(3)-Leu-Bth-Pro-D-AlaNH₂;

N-Ac-D-Nal(2)-D-pCl-Phe-D-Pal(3)-Ser-Arg-D-Pal(3)-Leu-Mbh-Pro-D-AlaNH₂;

N-Ac-D-Nal(2)-D-pCl-Phe-D-Pal(3)-Ser-Arg-D-Pal(3)-Leu-Deh-Pro-D-AlaNH₂;

N-Ac-D-Nal(2)-D-pCl-Phe-D-Pal(3)-Ser-Arg-D-Pal(3)-Leu-Pha-Pro-D-AlaNH₂;

N-Ac-D-Nal(2)-D-pCl-Phe-D-Trp-Ser-Arg-D-Tyr-Leu-Deh-Pro-D-AlaNH₂;

N-Ac-D-Nal(2)-D-pCl-Phe-D-Trp-Ser-Arg-D-Tyr-Leu-Bth-Pro-D-AlaNH₂;

N-Ac-D-Nal(2)-D-pCl-Phe-D-Trp-Ser-Arg-D-Tyr-Leu-Mbh-Pro-D-AlaNH₂;

N-Ac-D-Nal(2)-D-pCl-Phe-D-Trp-Ser-Arg-D-Tyr-Leu-Pha-Pro-D-AlaNH₂;

N-Ac-D-Nal(2)-D-pCl-Phe-D-Pal(3)-Ser-Arg-D-Tyr-Leu-Bth-Pro-D-AlaNH₂;

N-Ac-D-Nal(2)-D-pCl-Phe-D-Pal(3)-Ser-Arg-D-Tyr-Leu-Mbh-Pro-D-AlaNH₂;

N-Ac-D-Nal(2)-D-pCl-Phe-D-Pal(3)-Ser-Arg-D-Tyr-Leu-Deh-Pro-D-AlaNH₂;

N-Ac-D-Nal(2)-D-pCl-Phe-D-Pal(3)-Ser-Arg-D-Tyr-Leu-Pha-Pro-D-AlaNH₂; and or a pharmaceutically acceptable salt thereof.

21. A compound of claim 3 selected from the group consisting of:

N-Ac-D-Nal(2)-D-pCl-Phe-D-Trp-Ser-Deh-D-Tyr-Leu-Deh-Pro-D-AlaNH₂;

N-Ac-D-Nal(2)-D-pCl-Phe-D-Trp-Ser-Mbh-D-Tyr-Leu-Mbh-Pro-D-AlaNH₂;

N-Ac-D-Nal(2)-D-pCl-Phe-D-Trp-Ser-Bth-D-Tyr-Leu-Bth-Pro-D-AlaNH₂;

N-Ac-D-Nal(2)-D-pCl-Phe-D-Trp-Ser-Pha-D-Tyr-Leu-Pha-Pro-D-AlaNH₂;

N-Ac-D-Nal(2)-D-pCl-Phe-D-Trp-Ser-Deh-D-Trp-Leu-Deh-Pro-D-AlaNH₂;

N-Ac-D-Nal(2)-D-pCl-Phe-D-Trp-Ser-Mbh-D-Trp-Leu-Mbh-Pro-D-AlaNH₂;

N-Ac-D-Nal(2)-D-pCl-Phe-D-Trp-Ser-Bth-D-Trp-Leu-Bth-Pro-D-AlaNH₂;

N-Ac-D-Nal(2)-D-pCl-Phe-D-Trp-Ser-Pha-D-Trp-Leu-Pha-Pro-D-AlaNH₂;

N-Ac-D-Nal(2)-D-pCl-Phe-D-Pal(3)-Ser-Deh-D-Pal(3)-Leu-Deh-Pro-D-AlaNH₂;

N-Ac-D-Nal(2)-D-pCl-Phe-D-Pal(3)-Ser-Mbh-D-Pal(3)-Leu-Mbh-Pro-D-AlaNH₂;

N-Ac-D-Nal(2)-D-pCl-Phe-D-Pal(3)-Ser-Bth-D-Pal(3)-Leu-Bth-Pro-D-AlaNH₂;

N-Ac-D-Nal(2)-D-pCl-Phe-D-Pal(3)-Ser-Pha-D-Pal(3)-Leu-Pha-Pro-D-AlaNH₂;

N-Ac-D-Nal(2)-D-pCl-Phe-D-Trp-Ser-Deh-D-Nal(2)-Leu-Deh-Pro-D-AlaNH₂;

N-Ac-D-Nal(2)-D-pCl-Phe-D-Trp-Ser-Mbh-D-Nal(2)-Leu-Mbh-Pro-D-AlaNH₂;

N-Ac-D-Nal(2)-D-pCl-Phe-D-Trp-Ser-Bth-D-Nal(2)-Leu-Bth-Pro-D-AlaNH₂;

N-Ac-D-Nal(2)-D-pCl-Phe-D-Trp-Ser-Pha-D-Nal(2)-Leu-Pha-Pro-D-AlaNH₂;

N-Ac-D-Nal(2)-D-pCl-Phe-D-Pal(3)-Ser-Pal(3)-D-Pal(3)-Leu-Deh-Pro-D-AlaNH₂;

N-Ac-D-Nal(2)-D-pCl-Phe-D-Pal(3)-Ser-Pal(3)-D-Pal(3)-Leu-Bth-Pro-D-AlaNH₂;

N-Ac-D-Nal(2)-D-pCl-Phe-D-Pal(3)-Ser-Pal(3)-D-Pal(3)-Leu-Pha-Pro-D-AlaNH₂; and

N-Ac-D-Nal(2)-D-pCl-Phe-D-Pal(3)-Ser-Pal(3)-D-Pal(3)-Leu-Mbh-Pro-D-AlaNH₂;

or a pharmaceutically acceptable salt thereof.

22. A compound of claim 3 selected from the group consisting of:

N-Ac-D-Nal(2)-D-pCl-Phe-D-Pal(3)-Ser-Tyr-D-Pal(3)-Leu-Deh-Pro-D-AlaNH₂;

N-Ac-D-Nal(2)-D-pCl-Phe-D-Pal(3)-Ser-Mbh-D-Pal(3)-Leu-Mbh-Pro-D-AlaNH₂;

N-Ac-D-Nal(2)-D-pCl-Phe-D-Pal(3)-Ser-Pal(3)-D-Pal(3)-Leu-Bth-Pro-D-AlaNH₂;

N-Ac-D-Nal(2)-D-pCl-Phe-D-Pal(3)-Ser-Arg-D-Pal(3)-Leu-Deh-Pro-D-AlaNH₂;

N-Ac-D-Nal(2)-D-pCl-Phe-D-Pal(3)-Ser-Tyr-D-Pal(3)-Leu-Bth-Pro-D-AlaNH₂;

N-Ac-D-Nal(2)-D-pCl-Phe-D-Pal(3)-Ser-Tyr-D-Pal(3)-Leu-Mbh-Pro-D-AlaNH₂;

N-Ac-D-Nal(2)-D-pCl-Phe-D-Pal(3)-Ser-Tyr-D-Pal(3)-Leu-Pha-Pro-D-AlaNH₂;

N-Ac-D-Nal(2)-D-pCl-Phe-D-Trp-Ser-Tyr-D-Trp-Leu-Bth-Pro-D-AlaNH₂;

N-Ac-D-Nal(2)-D-pCl-Phe-D-Trp-Ser-Arg-D-Trp-Leu-Deh-Pro-D-AlaNH₂;

N-Ac-D-Nal(2)-D-pCl-Phe-D-Trp-Ser-Arg-D-Trp-Leu-Bth-Pro-D-AlaNH₂;

N-Ac-D-Nal(2)-D-pCl-Phe-D-Trp-Ser-Arg-D-Trp-Leu-Pha-Pro-D-AlaNH$_2$;
N-Ac-D-Nal(2)-D-pCl-Phe-D-Pal(3)-Ser-Arg-D-Pal(3)-Leu-Pha-Pro-D-AlaNH$_2$;
N-Ac-D-Nal(2)-D-pCl-Phe-D-Trp-Ser-Tyr-D-Bth-Leu-Bth-Pro-D-AlaNH$_2$;
N-Ac-D-Nal(2)-D-pCl-Phe-D-Trp-Ser-Tyr-D-Phe-Leu-Pha-Pro-D-AlaNH$_2$;
N-Ac-D-Nal(2)-D-pCl-Phe-D-Pal(3)-Ser-Tyr-D-Deh-Leu-Deh-Pro-D-AlaNH$_2$; and
N-Ac-D-Nal(2)-D-pCl-Phe-D-Pal(3)-Ser-Tyr-D-Bth-Leu-Bth-Pro-D-AlaNH$_2$;
or a pharmaceutically acceptable salt thereof.

23. A compound of claim 3 which is:
N-Ac-D-Nal(2)-D-pCl-Phe-D-Pal(3)-Ser-Tyr-D-Pal(3)-Leu-Deh-Pro-D-AlaNH$_2$;
or a pharmaceutically acceptable salt thereof.

24. A compound of claim 3 which is:
N-Ac-D-Nal(2)-D-pCl-Phe-D-Pal(3)-Ser-Tyr-D-Pal(3)-Leu-Bth-Pro-D-AlaNH$_2$;
or a pharmaceutically acceptable salt thereof.

25. A compound of claim 3 which is:
N-Ac-D-Nal(2)-D-pCl-Phe-D-Pal(3)-Ser-Tyr-D-Pal(3)-Leu-Mbh-Pro-D-AlaNH$_2$;
or a pharmaceutically acceptable salt thereof.

26. A compound of claim 3 which is:
N-Ac-D-Nal(2)-D-pCl-Phe-D-Pal(2)-Ser-Tyr-D-Pal(3)-Leu-Pha-Pro-D-AlaNH$_2$;
or a pharmaceutically acceptable salt thereof.

27. A compound of claim 3 which is:
N-Ac-D-Nal(2)-D-pCl-Phe-D-Trp-Ser-Tyr-D-Trp-Leu-Bth-Pro-D-AlaNH$_2$;
or a pharmaceutically acceptable salt thereof.

28. A compound of claim 3 which is:
N-Ac-D-Nal(2)-D-pCl-Phe-D-Trp-Ser-Arg-D-Trp-Leu-Bth-Pro-D-AlaNH$_2$;
or a pharmaceutically acceptable salt thereof.

29. A compound of claim 3 which is:
N-Ac-D-Nal(2)-D-pCl-Phe-D-Trp-Ser-Arg-D-Trp-Leu-Pha-Pro-D-AlaNH$_2$;
or a pharmaceutically acceptable salt thereof.

30. A compound of claim 3 which is:
N-Ac-D-Nal(2)-D-pCl-Phe-D-Pal(3)-Ser-Arg-D-Pal(3)-Leu-Bth-Pro-D-AlaNH$_2$;
or a pharmaceutically acceptable salt thereof.

31. A compound of claim 3 which is:
N-Ac-D-Nal(2)-D-pCl-Phe-D-Pal(3)-Ser-Arg-D-Pal(3)-Leu-Pha-Pro-D-AlaNH$_2$;
or a pharmaceutically acceptable salt thereof.

32. A compound of claim 3 which is:
N-Ac-D-Nal(2)-D-pCl-Phe-D-Pal(3)-Ser-Mbh-D-Pal(3)-Leu-Mbh-Pro-D-AlaNH$_2$;
or a pharmaceutically acceptable salt thereof.

33. A compound of claim 3 which is:
N-Ac-D-Nal(2)-D-pCl-Phe-D-Pal(3)-Ser-Pal(3)-D-Pal(3)-Leu-Bth-Pro-D-AlaNH$_2$;
or a pharmaceutically acceptable salt thereof.

34. A compound of claim 3 which is:
N-Ac-D-Nal(2)-D-pCl-Phe-D-Pal(3)-Ser-Arg-D-Pal(3)-Leu-Deh-Pro-D-AlaNH$_2$;
or a pharmaceutically acceptable salt thereof.

35. A pharmaceutical composition for inhibiting ovulation in a mammalian female subject; preventing ovarian hyperstimulation in response to exogenous gonadotropins, treating premenstrual syndrome, or treating endometriosis in a female human subject; for treating prostatic hypertrophy or inhibiting spermatogenesis in a male mammalian subject; or for treating precocious puberty in a human subject; or interrupting heat in a female animal; or terminating pregnancy in a female mammalian subject; comprising an effective amount of the compound of claim 1 in admixture with at least one pharmaceutically acceptable excipient.

36. A compound of claim 3 which is
N-Ac-D-Nal(2)-D-pCl-Phe-D-Pal(3)-Ser-Bth-D-Tyr-Leu-Bth-Pro-D-Ala-NH$_2$;
or an optical isomer thereof; or a pharmaceutically acceptable salt thereof.

37. The compound of claim 3 which is
N-Ac-D-Nal(2)-D-pCl-Phe-D-Trp-Ser-Tyr-D-Bth-Leu-Bth-Pro-D-AlaNH$_2$;
or an optical isomer thereof; or a pharmaceutically acceptable salt thereof.

38. The compound of claim 3 which is
N-Ac-D-Nal(2)-D-pCl-Phe-D-Trp-Ser-Tyr-D-Pha-Leu-Pha-Pro-D-AlaNH$_2$
or an optical isomer thereof; or a pharmaceutically acceptable salt thereof.

39. The compound of claim 3 which is
N-Ac-D-Nal(2)-D-pCl-Phe-D-Pal(3)-Ser-Tyr-D-Deh-Leu-Deh-Pro-D-AlaNH$_2$;
or an optical isomer thereof; or a pharmaceutically acceptable salt thereof.

40. The compound of claim 3 which is
N-Ac-D-Nal(2)-D-pCl-Phe-D-Pal(3)-Ser-Tyr-D-Bth-Leu-Bth-Pro-D-AlaNH$_2$;
or an optical isomer thereof; or a pharmaceutically acceptable salt thereof.

41. The compound of claim 3 which is
N-Ac-D-Nal(2)-D-pCl-Phe-D-Pal(3)-Ser-Mbh-D-Pal(3)-Leu-Mbh-Pro-D-AlaNH$_2$;
or an optical isomer thereof; or a pharmaceutically acceptable salt thereof.

* * * * *

UNITED STATES PATENT AND TRADEMARK OFFICE
CERTIFICATE OF CORRECTION

PATENT NO. : 4,801,577
DATED : Jan. 31, 1989
INVENTOR(S) : Nestor, Jr. et al.

It is certified that error appears in the above-identified patent and that said Letters Patent is hereby corrected as shown below:

Claim 2, at column 29, line 67 "A compound of claim 2 wherein:" should read -- A compound of claim 1 wherein --.

Signed and Sealed this

Fourth Day of January, 2000

Attest:

Attesting Officer

*Acting Commissioner of Patents and Trademarks*